United States Patent [19]

Bergquist

[11] Patent Number: 5,675,065

[45] Date of Patent: Oct. 7, 1997

[54] SYNTHETIC CORN HYBRID LP39

[76] Inventor: Richard R. Bergquist, 401 E. 6th St., El Paso, Ill. 61738

[21] Appl. No.: 470,001

[22] Filed: Jun. 6, 1995

[51] Int. Cl.$^6$ ............................... A01H 5/00; A01H 4/00; A01H 1/00; C12N 5/04

[52] U.S. Cl. ................ 800/200; 800/250; 800/DIG. 56; 435/240.4; 435/240.49; 435/240.5; 47/58; 47/DIG. 1

[58] Field of Search ........................... 800/200, 205, 800/250, DIG. 56; 47/58, DIG. 1; 435/172.3, 172.1, 240.4, 240.49

[56] References Cited

PUBLICATIONS

Aldrich et al., *Modern Crop Production*, 7–13, 46–49 (1982).
Alexander et al., Breeding Special Industrial and Nutritional Types, Chapter from *Corn and Corn Improvement*, Sprague ed., 363–370 (1977).
Allard, *Principles of Plant Breeding*, 166–303 (1960).
Crabb, *The Hybrid Corn Makers*, 229–243 (1991).
Creech et al., Breeding for Industrial and Nutritional Quality in Maize, Chapter in *Maize Breeding and Genetics*, Walden ed., 249–264 (1978).
Dudley et al., Seventy Generations of Selection for Oil and Protein Concentration in Maize, Chapter from *Seventy Generations of Selection for Oil and Protein in the Maize Kernel*, Dudley ed., 181–212 (1974).
Elliott, *Plant Breeding and Cytogenetics*, 260–302 (1958).
Frey, *Plant Breeding II*, 387–395 (1981).
Hayes et al., *Methods of Plant Breeding*, 267–346 (1955).
Orthoeffer et al., Corn Oil: Composition, Processing, and Utilization, Chapter from *Corn: Chemistry and Technology*, Watson et al., ed., 535–551 (1987).
Poehlman, *Breeding Field Crops*, 241–277 (1959).
Stoskopf et al., *Plant Breeding—Theory and Practice*, 1, 185–199, 219–237, 287–325 (1993).
Weber, Lipids of the Kernel, Chapter from *Corn: Chemistry and Technology*, Watson et al., ed., 311–348 (1987).

*Primary Examiner*—Gary Benzion
*Attorney, Agent, or Firm*—Bullwinkel Partners, Ltd.

[57] ABSTRACT

This invention is a synthetic hybrid corn plant having the designation LP39, produced by crossing two proprietary Pfister Hybrid Corn Company maize synthetics, LP39A-Reid and LP39B-Lancaster. LP39 has the unique property of imparting high oil and high protein levels in the grain of certain normal and male sterile hybrids when used as a pollinator; and in addition is characterized by excellent cold tolerant seedling vigor for rapid emergence in cold soils, and excellent early-season adaptability to nick with early maize hybrids that condition fast dry-down and superior grain quality in the recipient female grain parent. This invention thus relates to the synthetic hybrid plants and seeds of LP39, i.e., the synthetic hybrid produced by crossing the two aforementioned synthetics and the seed thereof, including advanced generation seed, variants, mutants, and modifications of LP39.

12 Claims, No Drawings

SYNTHETIC CORN HYBRID LP39

TABLE OF CONTENTS

Field of the Invention
Background of the Invention
  Uses of Corn
  Principles of Conventional Plant Breeding
  Synthetic Varieties
  The Desirability of High Oil Content Corn
  The TopCross™ Grain Production System
  Need for Superior Pollinators
Summary
  Description of LP39
  Advantages of LP39
Detailed Description of the Invention
  Definitions
  Development of LP39
  Characteristics
  Benefits of LP39 as a Pollinator
  EXAMPLES OF LP39'S USEFULNESS AS A POLLINATOR
    EXAMPLE I: Strip Test Grain Yields
    EXAMPLE II: Oil of TopCross™ Grain
    EXAMPLE III: Protein of TopCross™ Grain
    EXAMPLE IV: Moisture of TopCross™ Grain
    EXAMPLE V: Density of TopCross™ Grain
    EXAMPLE VI: Tassel-Silk Synchronization
    EXAMPLE VII: RAPD Data
  Deposit Information
Claims

FIELD OF THE INVENTION

This invention is in the field of plant breeding. Specifically, this invention relates to a novel synthetic corn hybrid having the designation LP39 and useful in the TopCross™ grain production system described in pending U.S. patent application Ser. Nos. 07/615,839 and 08/050,255 by Bergquist et al.

BACKGROUND OF THE INVENTION

TopCross™ is a trademark of the E. I. DuPont de Nemours and Company Inc. for grain produced by a method wherein male sterile corn plants are grown with and pollinated by corn plants which control the expression of desirable grain traits in the resulting grain, such as high oil and protein. A key requirement in the production of TopCross™ grain is the use of a suitable pollinator.

The present invention is a hybrid corn synthetic referred to hereinafter as LP39. LP39 was developed for use as a pollinator in producing TopCross™ grain having desirable grain quality traits. In addition, LP39 was developed to have superior agronomic characteristics to enhance its performance as a pollinator. LP39 was developed using standard plant breeding practices.

Uses of Corn

Corn (*Zea mays* L.) is an important crop used as a human food source, animal feed, and as a raw material in industry. The food uses of corn, in addition to the human consumption of corn kernels, include products of both the dry milling and wet milling industries. The principal products of dry milling include grits, meal and flour. The principal products of wet milling include starch, syrups, and dextrose. A by product of both dry and wet milling is corn oil, which is recovered from corn germ. As animal feed, corn is used primarily as a feedstock for beef cattle, dairy cattle, swine, poultry, and fish.

Industrial uses of corn mainly consist of the use of corn starch produced by wet milling and corn flour produced by dry milling and the whole kernel fermenation for production of food-grade and industrial use ethanol. The industrial applications of corn starch and flour are based on their functional properties, such as viscosity, film formation ability, adhesiveness, and ability to suspend particles. Corn starch and flour are used in the paper and textile industries, and as components in adhesives, building materials, foundry binders, laundry starches, explosives, and oil-well muds. Plant parts other than the corn kernels are also used in industry. For example, stalks and husks can be made into paper and wallboard, and corn cobs can be used for fuel and to make charcoal.

Principles of Conventional Plant Breeding

Virtually all of the commercial corn produced in the United States is produced from hybrid seed. The production of hybrid seed first requires the development of elite corn inbred lines that possess good combining ability to produce agronomically superior hybrids. The majority of hybrid seed produced in the United States is of the single cross type, wherein two inbred lines are intermated, or crossed, to produce what is termed an $F_1$ single cross hybrid. The resulting kernels from this intermating are then sold as seed to commercial growers who plant the seed and harvest the second generation, or $F_2$ grain, for use on farm or for commercial sale.

The production of a conventional single cross hybrid seed involves controlling the direction of pollination from one inbred to the other to assure the production of predominantly hybrid (cross pollinated) seed. Typically directed pollination is accomplished by interplanting separate rows of female corn plants with male corn plants. The female corn plants that are male sterile may be produced by genetic mechanisms which render the corn tassel nonfunctional or by detassling the plants in the field.

The development of corn hybrids requires the development of homozygous inbred lines or uniform synthetic populations of unique heterotic background, the crossing of these lines, and evaluation of test crosses. Pedigree breeding and recurrent selection breeding programs are used to develop inbred lines and synthetic populations from breeding populations. Breeding programs combine desirable traits from two or more inbred lines or various broad-based sources into breeding pools from which new inbred lines or synthetic populations are developed by inbreeding or random mating and selection of desired phenotypes. The new inbreds and/or synthetic lines are crossed with other inbred lines and/or synthetic populations and the hybrids from these crosses are evaluated to determine which have commercial value and agronomic usefulness.

Pedigree breeding starts with the crossing of two genotypes, each of which may have one or more desirable characteristics that is lacking in the other or which complements the other. If the two original genotypes do not provide all of the desired characteristics, other sources can be included during the breeding. In the pedigree breeding method, superior plants are selfed or random mated and the resulting seed selected in successive generations. Pedigree records of ancestry are carefully maintained for each family and ear row selection through succeeding generations. In the succeeding generations, the heterozygous condition of the corn germplasm gives way to homozygous true breeding lines as a result of inbreeding and selection. Typically in the pedigree method of breeding, five or more generations of inbreeding and selection is practiced: $F_1$ to $F_2$; $F_2$ to $F_3$; $F_3$ to $F_4$; $F_4$ to $F_5$, etc.

Backcrossing can be used to improve an inbred line by transferring a specific desirable trait from one inbred or source to another inbred that lacks that trait. This can be accomplished, for example, by first crossing a superior inbred (recurrent parent) to a donor inbred (nonrecurrent parent). The donor inbred carries (donates) the appropriate gene(s) for the desired trait to the next generation. After five or more backcross generations with selection for the desired trait, the inbred will be heterozygous for loci controlling the characteristic being transferred, but will be like the superior parent for most or almost all other genes. The last backcross generation can be selfed to produce a pure breeding progeny for the gene(s) being transferred.

An important consequence of the homozygosity and homogeneity of the inbred lines is that the hybrid between any two inbreds will always be the same. Once the inbreds or synthetics that give the best hybrid have been identified, the hybrid seed can be reproduced indefinitely as long as the homogeneity of the inbred or synthetic parents is maintained.

A synthetic hybrid consists of an array of similar genotypes that were identified from intercross tests and bulked into a random mating population having a desired phenotype. The intercrosses between two different heterotic groups results in the continuous production of a specific synthetic hybrid of desired phenotype.

As previously noted, a single cross hybrid is produced when two unrelated inbred or synthetic lines are crossed to produce the $F_1$ progeny. A three-way cross hybrid is produced from three inbred lines (or synthetics) where two of the inbred lines are crossed (A×B) and then the resulting $F_1$ hybrid is crossed with the third inbred (A×B)×C. A double cross hybrid is produced from four inbred lines (or synthetics) by crossing pairs (A×B) and (C×D) and then crossing the two $F_1$ hybrids (A×B)×(C×D).

Much of the hybrid vigor exhibited by $F_1$ hybrids is lost in the next generation ($F_2$). Consequently, seed from hybrid varieties is not used for planting stock.

The objective of typical plant breeding is to combine in a single variety/hybrid the desirable traits of the parental lines. For field crops such as corn, these desirable traits may include resistance to diseases and insects, tolerance for heat and drought, reducing time to crop maturity, and better agronomic quality. With mechanical harvesting of many crops, uniformity of plant characteristics such as germination time and stand establishment, growth rate, and fruit size is also desirable.

The problem with conventional breeding techniques is that there are several grain quality traits, such as high oil content, that cannot readily be combined in a high-yielding single cross hybrid. It is unique to the present invention that, when used as a pollinator, it imparts desirable grain quality characteristics, such as high oil content, to the resulting F1 grain without significant loss of yield. This heretofore was not possible because these desirable grain quality characteristics in hybrids usually have been associated with low yield and poor agronomic characteristics.

Synthetic Varieties

Corn has male flowers, located on the tassel, and female flowers, located on the ear, of the same plant. Because of this monoecy, corn plants can be bred by both self-pollination and cross-pollination techniques. Corn is self-pollinated if pollen from one flower is transferred to the same or another flower on the same plant. Corn is cross-pollinated if the pollen comes from a flower on a different plant.

Plants that have been self-pollinated and selected for uniform type over many generations become homozygous at almost all gene loci and produce a uniform population of true breeding progeny. Cross pollination between two homozygous lines produces a uniform population of hybrid plants that nevertheless may be heterozygous for many gene loci. A cross between two plants that are each heterozygous for a number of gene loci will produce a population of hybrid plants that differ genetically and will not be uniform.

Natural pollination occurs when wind blows pollen from tassels to silks that protrude from tops of the incipient ears on plants of the same genotype and different genotype, resulting in both self- and cross-pollination. When a population of genotypes are combined from all possible intercrosses among a number of selected genotypes and are allowed to open pollinate, the result is called a synthetic variety. A synthetic variety is made up of genotypes which previously have been tested for their ability to produce a superior progeny when crossed in all combinations.

Corn plants may be maintained as an outcrossing synthetic population that is much less homogeneous than a self-pollinated group. Every plant in such a group is certain to be heterozygous, and this heterozygosity must either be maintained during a breeding program or restored at the end of the program, if productivity is to be satisfactory. The main requirement in maintaining a synthetic line is that a sufficient number of plants of heterozygous background be maintained to recover the gene frequencies that are desired for the synthetic population so as to prevent genetic drift toward undesired gene frequencies.

The Desirability of High Oil Content Grain

The concentration of oil in most varieties of corn ranges from less than 3.0 percent to 4.5 percent at 0% moisture. Embryos of ordinary corn can contain 30 percent oil, while embryos of high oil corn strains can contain as much as 50 percent oil and are much larger in size than ordinary corn embryos.

There are several reasons for wanting to develop a method for growing corn that is high in oil content. First, corn oil is a premium oil and regularly more valuable than starch, the other major component of corn kernels. Second, high oil corn possesses a higher available energy content than ordinary corn, and thus is a more valuable feed for poultry and livestock. In animal feeding trials it has been found that less high oil corn is required per unit of gain than is required with ordinary corn. In addition, high oil corn requires substantially less soybean meal to balance a typical animal diet.

Additional impetus was given to breeding corn for high oil by the development of wide-line nuclear magnetic resonance spectroscopy (NMR) and near-infrared spectroscopy (NIR) as analytical tools for the nondestructive analysis of bulk or single kernel samples that can be carried out in as little as two seconds. The development of such tools made it much easier and much quicker to determine the oil content of grain, thereby encouraging experimentation in the area of breeding for high oil.

Thus there exists at present a growing market for corn having high oil, increased protein and other special end-use properties which is not met by corn of standard composition. The diverse types of corn available to plant breeders provides a potential for modification of quality and quantity of grain protein, starch, and oil. Corn now can be developed to more precisely meet the specific nutritional requirements of animals or to meet particular industrial needs.

The TopCross™ Grain Production System

Unfortunately, high oil is a property that cannot readily be achieved in a high yielding single-cross hybrid. This is because oil content, while being a moderately heritable trait, is influenced by a series of oil genes that have varying effects on oil content and occur at a complex of loci in at least eight linkage groups that influence the amount of oil in the grain progeny. Obtaining a hybrid having all or most of these oil genes can take many years of breeding. Further increasing the difficulty of breeding for high oil content is the fact that the grain yield of higher oil hybrids is generally inferior when compared to elite dent corn hybrids.

A method of producing a high yield of corn having high oil content without requiring years of breeding is described in Bergquist et al. U.S. patent application Ser. No. 07/615, 839. The primary aspect of this method, known as the TopCross™ grain production system, is the interplanting of a pollinator corn plant possessing the characteristics for significantly increasing oil and protein levels in the resulting grain with a male sterile hybrid corn plant. The resulting grain possesses an oil content much higher than would be expected for self- or cross-pollination of the fertile version of the hybrid corn plant.

In practice, the seed of the pollinator with improved grain quality traits is blended in small amounts with seed of an elite male sterile grain parent hybrid, but with sufficient pollinator seed to permit abundant pollen production for fertilization of the male sterile grain parent hybrid. The relatively low ratio of pollinator seed to male sterile grain parent seed (less than one pollinator plant to every three grain parent plants) takes advantage of the higher grain yield potential of the elite grain parent hybrid while assuring a sufficient population of pollinator plants to pollinate the male sterile grain parent plants.

Need for Superior Pollinators

Critical to the success of the TopCross™ grain production system is the use of a pollinator capable of enhancing the grain quality traits of the $F_1$ offspring. To obtain such pollinators, the corn breeder must select and develop corn plants that have the traits that result in superior inbred and synthetic parental lines.

The pollinator for the TopCross™ grain production system need not be genetically homozygous (inbred) or even uniform in appearance, and need not be selected for genetic combining ability with female plants. However, the pollinator should have uniform desirable grain quality characteristics, such as high oil, that will influence the grain quality characteristics of the $F_1$ offspring, and the ability to pollinate the female plants. A hybrid obtained by crossing two synthetic populations of different heterotic backgrounds results in a synthetic hybrid with predictable heterozygosity and genetic variability among plants that is particularly useful as a male pollinator in 8 to 20 percent commercial blends with male sterile hybrid grain parents in the TopCross™ grain production system. Some genetic variability is desirable because it extends the flowering period of the pollinator. LP39 was developed to achieve these characteristics.

SUMMARY

Description of LP39

This invention is a novel synthetic corn hybrid, designated LP39, that when used to pollinate an elite male sterile hybrid grain parent, produces commercial grain exhibiting improved quality grain traits, including high oil and protein. My invention thus relates to the seeds and plants of LP39, and to a method of producing LP39 by crossing synthetic LP39A-Reid and LP39B-Lancaster synthetics.

Thus it is an object of this invention to provide a synthetic hybrid corn plant having the designation LP39.

A further object of this invention is to provide a synthetic hybrid corn plant that, when used to pollinate an elite male sterile hybrid grain parent, produces a commercial grain expressing improved grain quality traits, including higher oil and protein contents.

A still further object of the invention is to provide a method of producing the synthetic hybrid corn plant LP39 by crossing LP39A-Reid and LP39B-Lancaster synthetics.

Advantages of LP39

The use of synthetic hybrids (such as LP39) as TopCross™ grain production system pollinators has unique advantages over using hybrids produced from single crosses. For instance, synthetic hybrids can be developed more rapidly than commercial hybrids. The use of a synthetic population can more rapidly establish stability of dominant oil genes, thereby by-passing the many generations of inbreeding that is required to produce inbreds for making single cross hybrids.

Second, synthetic hybrids often have excellent vigor comparable to that of commercial hybrids. Inbreds, by contrast, typically lose vigor with each successive generation of inbreeding. This is an important advantage of synthetics because pollinator vigor is critical for ample pollen shed at the time of silking in the TopCross™ grain production system. Synthetic hybrid LP39 expresses cold vigor in seedling growth stages greater than even most open pollinated synthetic populations.

Third, a synthetic variety, utilizing heterosis in which pollination control is a factor, is more likely to disperse pollen over a longer period of time than a single cross hybrid. The predictable greater variability of synthetic varieties as compared with single crosses permits more flexibility to meet the changing growing conditions typical of field production. In addition, because of the longer flowering period, fewer synthetic pollinators need be developed to be used in blends with many different grain parents.

Fourth, the synthetic hybrid pollinator is more easily produced during periods of heat and drought stress on dryland production than a single-cross hybrid using less vigorous inbred seed stocks. For example, in non-irrigated dryland field tests conducted during 1993 and 1994, production of synthetic hybrid seed remained relatively constant at about 55 bushels per acre despite the fact that rainfall accumulation during the critical months of May, June and July fell from 40.84 cm in 1993 to 13.82 cm in 1994. Over the same period, single cross seed production using inbred seed stocks fell to less than 25 bushels per acre in 1994 from 55 bushels per acre in 1993.

DETAILED DESCRIPTION OF THE INVENTION

1. Definitions

In the description and examples that follow, a number of terms are used herein. In order to provide a clear and consistent understanding of the specification and claims, including the scope to be given such terms, the following definitions are provided:

Adaptation. The process by which individuals (or parts of individuals) or populations change in form or function to better survive under given environmental conditions. Also the result of this process.

Anthesis. The period or act of flowering.

Backcross. The cross of a hybrid to either one of its parents. The offspring of such a cross is referred to as the backcross generation.

Backcross Method of Breeding. A system of breeding carried out by several generations of backcrossing to one of the parents of a hybrid and subsequent selection. The characteristics of the recurrent parent are retained for the most part, and characteristics from the nonrecurrent parent are added.

Barren Plants. Plants that lack ears, typically measured in number of plants per plot.

Brittle Stalks. This is a measure of the stalk breakage near the time of pollination of the hybrids, and is an indication of whether a hybrid would snap or break at the time of flowering under severe winds.

Bulk Method of Breeding. The growing of segregating generations of a hybrid of self-pollinating crops in a bulk, with or without mass selection, followed by individual plant selection in $F_6$ or later generations.

Cob Score. The cob score is a rating of how well the grain is shelled off the cob and how badly the cob is broken up going through the combine. A high score indicates that the grain shells off of the cob well, and the cob does not break.

Cytoplasmic Inheritance. Transmission of hereditary characters through the cytoplasm as distinct from transmission by genes carried by chromosomes. Detected by differing contribution of male and female parents in reciprocal crosses.

Diallel Cross. The crossing in all possible combinations of a series of genotypes.

Donor parent. The parent from which one or a few genes are transferred to the recurrent parent in backcross breeding.

Dropped Ears. This is a measure of the number of dropped ears per plot and represents the number of plants that did not drop ears prior to harvest.

Ear Height. The ear height is a measure from the ground to the top developed ear node attachment and is measured in centimeters.

Early Stand Count. This is a measure of the stand establishment in the spring and represents the number of plants that emerge on a per-plot basis for the hybrid.

Embryo. The rudimentary plant in a seed. The embryo arises from the zygote. In high oil corn breeding, increases in oil content are accompanied by increases in embryo size.

Endosperm. The nutritive tissue formed within the embryo sac in seed plants. It commonly arises following the fertilization of the two primary endosperm nuclei of the embryo sac by the two male sperms. In a diploid organism the endosperm is triploid.

Expressivity. The degree of manifestation of a genetic character.

$F_1$. The first generation of a cross.

$F_2$. The second filial generation obtained by self-fertilization or crossing inter se of $F_1$ individuals.

$F_3$. Progeny obtained by self-fertilizing $F_2$ individual. Subsequent generations $F_4$, $F_5$, etc.

GDD Shed. The GDD is the number of growing degree days (GDD) or heat units required for an inbred line or hybrid to reach anthesis or pollen shed from the time of planting. Growing degree days are calculated by the Barger Method, where the heat units for a 24-hour period are:

$$GDD = \frac{(Max. + Min.)}{2} - 50$$

The highest maximum used is 86 degrees F. and the lowest minimum used is 50 degrees F. For each hybrid it takes a certain number of GDDs to reach various stages of plant development. GDDs are a way of measuring plant maturity.

Genotype. The fundamental genetic constitution of an organism.

Grain Quality. This is a 1 to 5 rating for the general quality of the shelled grain as it is harvested based on the color of the harvested grain, any mold on the grain, and any cracked grain. Low scores indicate good grain quality.

Grain Quality Trait. This is any attribute of grain that is of commercial value. Such traits relate to the intermediate or final use of grain and include but are limited to the quantity or quality of oil, protein, starch, pigmentation, and fiber found in corn grain. Such traits also encompass physical attributes of the grain itself, such as grain texture, size, or hardness, among others. Certain of these compositional or physical attributes of grain correlate with functional attributes as well which are of commercial importance, such as susceptibility to breakage and spoilage, among others.

Hybrids. (1) The progeny of a cross fertilization between parents belonging to different genotypes. (2) The first generation offspring of a cross between two individuals differing in one or more genes. (3) A hybrid is the result of a cross between two or more components.

Hybrid Vigor. The phenomenon in which the cross of two stocks produce hybrids that show increased vigor-heterosis compared to the parent stocks.

Inbred Lines. (1) A line produced by continued inbreeding. In plant breeding a nearly homozygous line usually originating by continued self-fertilization, accompanied by selection. (2) A relatively homozygous line produced by inbreeding and selection.

LP39. A novel synthetic corn hybrid having superior agronomic characteristics and the ability to impart desirable grain quality traits to a first generation grain when used as a pollinator in the TopCross™ grain production system, and the later generation synthetic corn hybrids derived from it.

Male Sterility. A condition in which pollen is absent or non-functional in flowering plants.

MN RM. This represents the Minnesota Relative Maturity Rating (MN RM) for the hybrid and is based on the harvest moisture of the grain relative to a standard set of checks of previously determined MN RM rating. Regression analysis is used to compute this rating.

Moisture. The moisture is the actual percentage moisture of the grain at harvest.

Multiple Genes. Two or more independent pairs of genes which produce complementary or cumulative effects upon a single character of the phenotype.

Pedigree. A record of the ancestry of an individual, family, or strain.

Pedigree Breeding. A system of breeding in which individual plants are selected in the segregating generations from a cross on the basis of their desirability and on the basis of a pedigree record.

Penetrance. (1) The proportion of organisms heterozygous for a particular dominant gene or homozygous for a recessive which shows the phenotype under a set of specified environmental conditions; (2) complete penetrance is the situation in which a dominant gene always produces a phenotypic effect or a recessive gene in the homozygous state always produces a detectable effect; (3) the frequency with which a gene produces a recognizable effect in individuals which carry it.

Percent Yield. The percent yield is the yield obtained for the hybrid in terms of percent of the mean for the experiments in which it was grown.

Phenotype. (1) Physical or external appearance of an organism as contrasted with its genetic constitution (=genotype); (2) a group of organisms with similar physical or external makeup; (3) the observed character of an individual without reference to its genetic nature.

Plant Height. This is a measure of the height of the hybrid from the ground to the tip of the tassel and is measured in centimeters. The data is given in percentage of mean of the experiments in which the hybrid was grown.

Pollinator. Male fertile corn plants that are used to pollinate male sterile hybrid corn plants.

Population. In genetics, a community of individuals which share a common gene pool. In statistics, a hypothetical and infinitely large series of potential observations among which observations actually made constitute a sample.

Predicted R.M. Predicted relative maturity is based on the harvest moisture of the grain. The relative maturity rating (R.M.) is based on a known set of checks and utilizes standard linear regression analyses referred to as the Minnesota Relative Maturity Rating System.

Quantitative Character. A character in which variation is continuous so that classification into discrete categories is not possible. Also, a character determined by a series of independent genes which are cumulative in their effect.

Recurrent Parent. Used in backcrosses to refer to the parent to which the first cross and successive backcrossed plants are crossed.

Root Lodging. The percentage of plants that root lodge; i.e., those that lean from the vertical axis at an approximately 30 degree angle or greater would be counted as root lodged.

Seedling Vigor. This is the visual rating (1 to 5) of the amount of vegetative growth after emergence at the seedling stage (approximately five leaves). A higher score indicates better vigor.

Selection Index. The selection index gives a single measure of a hybrids's worth based on information for up to five traits. A corn breeder may utilize his or her own set of traits for the selection index. One of the traits that is almost always included is yield.

Self-fertilization. The fusion of the female egg cell of one individual with a male sperm cell of the same individual.

Sibs: Progeny of the same parents derived from different gametes. Half sibs, progeny with one parent in common.

Single Cross. A cross between two genotypes, usually two genetically different inbred lines or synthetic lines.

Stalk Lodging. This is the percentage of plants that do not stalk lodge, i.e., stalk breakage, as measured by either natural lodging or pushing the stalks and determining the percentage of plants that break off below the ear. This is a relative rating of a hybrid to other hybrids for standability.

Stay Green. Stay green is the measure of plant health near the time of black layer formation (physiological maturity). A low score on a scale of 1 to 5 indicates better late-season plant health.

Synthetic Variety. A variety produced by crossing inter se a number of genotypes selected for good combining ability in all possible hybrid combinations, with subsequent maintenance of the variety by open pollination.

Test Cross. A cross of a double or multiple heterozygote to the corresponding multiple recessive to test for homozygosity or linkage.

Test Weight. This is the measure of the weight of the grain in pounds for a given volume (bushel) adjusted for percent moisture.

Topcross. (1) A cross of a hybrid or synthetic or inbred to a multiple heterozygote of opposite corresponding multiple loci to obtain traits observed in the pollen donor parent; (2) a cross between a selection line, clone, etc., and a common pollen parent which may be a variety, inbred line, single cross, etc. The common pollen parent is called the topcross or tester parent. (3) In corn, a topcross is commonly an inbred-variety cross, an outcross of selections, clones, lines, or inbreds, to a common pollen parent.

TC Blend™. A trademark of E. I. DuPont de Nemours and Company, Inc. for a physical seed mixture of pollinator seed and male sterile grain parent seed meeting specific quality criteria.

TopCross™ Grain. The grain which results from the planting of TC Blend™ seed and having improved nutrient composition and grain quality. TopCross™ is trademark of E. I. DuPont de Nemours and Company, Inc. for grain produced by the TopCross™ grain production system.

TopCross™ Grain Production System. A method of commercial corn production whereby a low yielding male fertile corn pollinator is blended at 8 to 20 percent of the total seed count with an elite high yielding male sterile hybrid grain parent and allowed to pollinate the male sterile grain parent to produce TopCross™ grain having increased food and feed nutritional value, thus capitalizing on the high yield potential of the male sterile hybrid grain parent while contributing the grain quality traits from the fertile pollinator.

Variety. A subdivision of a species. A group of individuals within a species which are distinct in form or function from other similar arrays of individuals.

Yield (Bushels/Acre). The yield in bushels/acre is the actual yield of the grain at harvest adjusted to 15.5% moisture.

2. Development of LP39

LP39 is a yellow dent corn, high oil single cross synthetic hybrid, produced by the single cross of Pfister Hybrid Corn Company proprietary synthetic populations LP39A-Reid and LP39B-Lancaster. The method of producing LP39 is summarized in the following Table 1 and described in detail below.

TABLE 1

DEVELOPMENT OF LP39

| Season/Year | Generation | Pedigree Grown | Heterotic Group | Days to Tassel | GP Oil | Percent Oil Self | Percent Oil TC | No. Ears Saved |
|---|---|---|---|---|---|---|---|---|
| Summer 1990 | F1 | LH132 × ASKC28 | Reid | — | 3.2 | — | 8.44 | 15 |
|  | F1 | NC282 × ASKC28 | Reid | — | 3.4 | — | 8.74 | 2 |
|  | F1 | LH51 × ASKC28 | Lancaster | — | 3.1 | — | 7.13 | 10 |

TABLE 1-continued
DEVELOPMENT OF LP39

| Season/Year | Generation | Pedigree Grown | Heterotic Group | Days to Tassel | GP Oil | Percent Oil Self | Percent Oil TC | No. Ears Saved |
|---|---|---|---|---|---|---|---|---|
| Winter 1990–91 | F2 | LH132 × ASKC28 | Reid | — | — | 9.16 | — | 6 |
| | F2 | NC282 × ASKC28 | Reid | — | — | 8.64 | — | 5 |
| | F2 | LH51 × ASKC38 | Lancaster | — | — | 8.49 | — | 5 |
| | BC1-ASKC28 | (F1LH132 × ASKC28)ASKC28 | Reid | — | — | — | 12.26 | 1 |
| | BC1-ASKC28 | (F1LH51 × ASKC28)ASKC28 | Lancaster | — | — | — | 10.94 | 5 |
| Summer 1991 | BC2-ASKC28 | ASKC28(LH132 × ASKC28)ASKC28 | Reid | 63 | — | — | 17.18 | 11 |
| | BC1-ASKC28 | ASKC28(F2LH132 × ASKC28) | Reid | 63 | — | — | 12.26 | 1 |
| | BC1-ASKC28 | ASKC28(F2NC282 × ASKC28) | Reid | 62 | — | — | 15.22 | 4 |
| | BC2-ASKC28 | ASKC28(LH51 × ASKC28)ASKC28 | Lancaster | 62 | — | — | 17.40 | 8 |
| Winter 1991–92 | F1-Sib | (ASKC28(LH132 × ASKC28)ASCK28) | Reid | — | — | 16.05 | — | 48 |
| | F1-Sib | ASKC28(LH132 × ASKC28) | Reid | — | — | 14.57 | — | 44 |
| | F1-Sib | (ASKC28(F2NC282 × ASKC28)) | Reid | — | — | 13.50 | — | 43 |
| | F1-Sib | (ASKC28(LH51 × ASKC28)ASKC28) | Lancaster | — | — | 14.79 | — | 67 |
| | F2 | (ASKC28(LH132 × ASKC28)ASKC28) | Reid | — | — | 15.19 | — | 56 |
| | F2 | ASKC28(LH132 × ASKC28) | Reid | — | — | 15.06 | — | 46 |
| | F2 | (ASKC28(F2NC282 × ASKC28)) | Reid | — | — | 13.49 | — | 39 |
| | F2 | (ASKC28(LH51 × ASKC28)ASKC28 | Lancaster | — | — | 14.56 | — | 71 |
| Summer 1992 | F2 | (ASKC28(LH132 × ASKC28)ASKC28)-S | Reid | 72 | 4.07 | 15.18 | 8.06 | 309 |
| | F2 | ASKC28(F2LH132 × ASKC28)-S | Reid | 71 | 4.07 | 14.57 | 8.10 | 44 |
| | F2 | (ASKC28(LH51 × ASKC28)ASKC28)-S | Lancaster | 71 | 4.07 | 13.05 | 9.05 | 137 |
| | F3 | (ASKC28(LH132 × ASKC28)ASKC28) | Reid | 70 | 4.07 | 16.60 | 8.30 | 29 |
| | F3 | ASKC28(LH132 × ASKC28) | Reid | 71 | 4.07 | 11.80 | 9.20 | 43 |
| | F3 | (ASKC28(F2NC282 × ASKC28)) | Reid | 69 | 4.07 | 13.40 | 8.00 | 267 |
| | F3 | (ASKC28(LH51 × ASKC28)ASKC28) | Lancaster | 71 | 4.07 | 10.27 | 8.50 | 304 |
| Winter 1992–93 | EARLY GENERATION TESTING SERIES: | | | | | | | |
| | Diallel | 45 Diallel Crosses, 10 Familes | Reid-A | — | — | — | — | 450 |
| | Diallel | 45 Diallel Crosses, 10 Families | Lancaster-B | — | — | — | — | 450 |
| | F1 | 100 Intercrosses-A × B | LP39 | — | — | — | — | 1000 |
| | GENERAL COMBINING ABILITY TEST CROSSES | | | | | | | |
| | F1 | LH82 × Reid-A Group-10 Families | Reid | | | | | 200 |
| | F1 | LH132 × Lancaster-B Group-10 Families | Lancaster | | | | | 200 |
| | EARLY/LATE GENERATION INBREEDING SERIES | | | | | | | |
| | | Reid-A Group | | | | | | |
| | F4 | ASKC28(F2LH132 × ASKC28) | 1 | — | 3.92 | 12.60 | 7.00 | 8 |
| | F3 | ASKC28(F2LH132 × ASKC28)S | 10 | — | 3.92 | 15.20 | 7.40 | 7 |
| | F4 | ASKC28(LH132 × ASKC28)ASKC28 | 2, 6 | — | 3.92 | 14.30 | 7.70 | 18 |
| | F3 | ASKC28(LH132 × ASKC28)ASKC28-S | 3, 4, 5, 9 | — | 3.92 | 15.60 | 7.40 | 56 |
| | F4 | ASKC28(F2NC282 × ASKC28) | 7, 8 | — | 3.92 | 13.10 | 7.10 | 26 |
| | | Lancaster-B Group | | | | | | |
| | F3 | ASKC28(LH51 × ASKC28)ASKC28-S | 1, 6, 7, 8, 9, 10 | — | 3.92 | 13.40 | 7.20 | 65 |
| | F4 | ASKC28(LH51 × ASKC28)ASK28 | 2, 3, 4, 5 | — | 3.92 | 12.00 | 7.30 | 36 |
| Summer 1993 | EARLY/LATE GENERATION INBREEDING SERIES | | | | | | | |
| | | Reid-A Group | | | | | | |
| | F5 | ASKC28(LH132 × ASKC28) | 1 | 68 | 5.34 | 10.10 | 7.70 | 3 |
| | F4 | ASKC28(LH132 × ASKC28)-S | 10 | 65 | 5.34 | 12.80 | 8.10 | 10 |
| | F5 | ASKC28(LH132 × ASKC28)ASKC28 | 2, 6 | 65 | 5.34 | 11.50 | 8.60 | 11 |
| | F4 | ASKC28(LH132 × ASKC28)ASKC28-S | 3, 4, 5, 9 | 65 | 5.34 | 14.80 | 8.20 | 27 |
| | F5 | ASKC28(F2NC282 × ASKC28) | 7, 8 | 63 | 5.34 | 11.50 | 8.20 | 18 |
| | | Lancaster-B Group | | | | | | |
| | F4 | ASKC28(LH51 × ASKC28)ASKC28-S | 1, 6, 7, 8, 9, 10 | 68 | 5.34 | 11.40 | 8.30 | 27 |
| | F5 | ASKC28(LH51 × ASKC28)ASKC28-S | 2, 3, 4, 5 | 67 | 5.34 | 8.00 | 8.20 | 7 |
| | Random Mate | LP39A-RM1 | Reid | | | | | 20,000 |
| | | LP39B-RM1 | Lancaster | | | | | 20,000 |
| | Yield Tests | LP39 A × B Intercross Yield Test | | | | | | |
| | | LH51 × LP39A Single Cross Yield Tests | | | | | | |
| | | LH132 × LP39B Single Cross Yield Tests | | | | | | |
| | | LP39 TopCross Blends Strip Test | | | | | | |
| Winter 1993–94 | EARLY GENERATION TESTING SERIES | | | | | | | |
| | Random Mate-2 | LP39A-RM2 | Reid-A | | | | | 20,000 |
| | Random Mate-2 | LP39B-RM2 | Lancaster-B | | | | | 20,000 |
| | F1 | LP39A-RM2 × LP39B-RM2 | LP39 | | | | | 20,000 |
| | LATE GENERATION TESTING SERIES | | | | | | | |
| | Diallel | 45 Diallel Crosses, 10 Families | Reid-A | 62 | — | 15.30 | 8.00 | 569 |

TABLE 1-continued

DEVELOPMENT OF LP39

| Season/Year | Generation | Pedigree Grown | Heterotic Group | Days to Tassel | GP Oil | Percent Oil Self | Percent Oil TC | No. Ears Saved |
|---|---|---|---|---|---|---|---|---|
| | Diallel | 45 Diallel Crosses, 10 Families | Lancaster-A | 63 | — | 12.60 | 8.30 | 459 |
| | F1 | 100 Intercrosses, A × B | LP39.1 | — | — | — | — | 1000 |
| | LATE GENERATION INBREEDING SERIES | | | | | | | |
| | | REID-A GROUP | | | | | | |
| | F5 | ASKC28(LH132 × ASKC28)S | 1, 9, 10 | 54 | — | — | — | 45 |
| | F6 | ASKC28(LH132 × ASKC28)ASKC28 | 2, 6 | 53 | — | — | — | 39 |
| | F5 | ASKC28(LH132 × ASKC28)ASK28-S | 3, 4, 5 | 53 | — | — | — | 71 |
| | F6 | ASKC28(NC282 × ASKC28) | 7, 8 | 53 | — | — | — | 22 |
| | | LANCASTER-B GROUP | | | | | | |
| | F5 | ASKC28(LH51 × ASKC28)ASKC28-S | 1, 6, 7, 8, 9, 10 | 53 | — | — | — | 263 |
| | F6 | ASKC28(LH51 × ASKC28)ASKC28 | 2, 3, 4, 5 | 53 | — | — | — | 135 |
| Summer 1994 | LATE GENERATION INBREEDING SERIES | | | | | | | |
| | | REID-A GROUP | | | | | | |
| | F7 | ASKC28(LH132 × ASKC28) | 1, 9, 10 | 67 | 3.20 | 13.60 | 7.60 | 89 |
| | F7 | ASKC28(LH132 × ASKC28)ASKC28 | 2, 6 | 66 | 3.20 | 13.70 | 7.90 | 103 |
| | F6 | ASKC28(LH132 × ASKC28)ASKC28-S | 3, 4, 5 | 64 | 3.20 | 16.40 | 7.80 | 153 |
| | F7 | ASKC28(NC282 × ASKC28) | 7, 8 | 65 | 3.40 | 12.90 | 7.10 | 116 |
| | | LANCASTER-B GROUP | | | | | | |
| | F6 | ASKC28(LH51 × ASKC28)ASKC28-S | 1, 6, 7, 8, 9, 10 | 70 | 3.10 | 12.30 | 8.20 | 264 |
| | F7 | ASKC28(LH51 × ASKC28)ASKC28 | 2, 3, 4, 5 | 69 | 3.10 | 11.40 | 7.50 | 199 |
| | Random Mate | | | | | | | |
| | RM3 | LP39A-RM3 | Reid | | | | | 80,000 |
| | RM3 | LP39B-RM3 | Lancaster | | | | | 80,000 |
| | RM1 | LP39A-RM1 (LG) | Reid | | | | | 20,000 |
| | RM1 | LP39B-RM1 (LG) | Lancaster | | | | | 20,000 |
| | HYBRID PROD. | | | | | | | |
| | F1 | LP39B-RM2 × LP39A-RM2 | LP39 | | | | | |
| | Yield Tests | TopCross Blends Strip Tests | LP39, LP39.1 | | | | | |

Summer 1990: Initial Crosses

Both parents of LP39, LP39A and LP39B, originated from three initial crosses that were made at El Paso, Ill. in the summer of 1990. In one cross, ASKC28, a high oil synthetic, was crossed to Reid inbred LH132, a proprietary inbred of Holden's Foundation Seed Company. In a second cross, ASKC28 was crossed to Reid inbred NC282, a licensed inbred from University of North Carolina. In a third cross, ASKC28 was crossed to Holden's Lancaster LH51 inbred. Each cross produced an F1 single cross population.

Winter 1990–91: Inbreeding and Backcross-One with ASKC28

In winter 1990–91, the three $F_1$ single cross populations were selfed and two were backcrossed by ASKC28 at Molokai, Hi. The selfs are designated $F_2$(LH132×ASKC28), $F_2$(NC282×ASKC28), and $F_2$(LH51×ASKC28) in Table 1. The two backcross populations (referred to as backcross-one populations) were produced by backcrossing ASKC28 to the $F_1$ generation of LH132×ASKC28 and LH51×ASKC28 lines.

Summer 1991: Backcross-Two with ASKC28

In summer of 1991, the two ASKC28 backcross-one populations, (LH132×ASKC28)ASKC28 and (LH51× ASKC28)ASKC28, and the $F_2$ generations from $F_2$LH132× ASKC28 and $F_2$NC282×ASKC28 were each backcrossed to ASKC28 as the female grain parent, producing backcross-two (BC2) and backcross-one (BC1), respectively. ASKC28 was used as the female parent to re-establish the ASKC28 cytoplasm for maintenance of high oil. Superior plants, identified in the backcross-one generation and $F_2$ populations with the desirable traits from the normal oil dent inbreds, were backcrossed to ASKC28 as female to insure recovery of its cytoplasm. An increase in oil was observed from the cytoplasmic effects resulting from this cross. The backcross method was considered most useful for introducing the favorable dominant oil genes from ASKC28 into the Reid and Lancaster heterotic groups while maintaining the agronomically useful characteristics from the normal-oil dent inbreds.

Winter 1991–92: Inbreeding and Random Mating Generations

In winter of 1991–92, each of the three heterotic backcross populations from the previous summer generation were pollinated by selfing and sib-mating in a one on one breeding system to identify plants with complementary dominant oil genetic linkage groups within a heterotic group. Selfing was accomplished by pollinating silks with pollen from tassels on the same plant. Sibbing, or random mating, was accomplished by pollinating silks from one plant with pollen from a tassel of another plant within the same heterotic population. Ears from the selfed plants are designated $F_2$ in Table 1, and ears from the sib-mated plants are designated $F_1$-Sib.

The purpose of sibbing was to recombine the oil gene linkage groups to ultimately pyramid the complex array of oil genes into a smaller number of plants which were later identified through test crosses that determine the level of increased oil of TopCross™ grain.

Summer 1992: Inbreeding and Testing

In summer of 1992, approximately 1,000 plants from the seven ASKC28 backcross populations from the previous sibbed and inbreeding generations were inbred to $F_2$ and $F_3$ and concurrently crossed to two testers, A632wx and Pfister Hybrid 3000, to identify normal grain type segregants with favorable dominant oil genes by analysis of the TopCross™ grain.

The $F_2$ and $F_3$ progenies from sibbed or selfed populations were selfed and testcrossed to: (1) a hybrid tester for identification of dominant complementary genetic patterns conditioning high oil in TopCross™ grain, and (2) a waxy grain tester to identify homozygous normal grain segregants and evaluated at Pfister Hybrid Corn Company's El Paso research station.

Winter 1992–93: Production of Early Generation Testing Series LP39 and Inbreeding of Selected Populations for Late Generation Development of LP39

The procedure for producing the LP39 synthetic hybrid with A-Reid and B-Lancaster conversion populations for an early generation testing series was as follows. Approximately 1,000 plants from the Reid and Lancaster heterotic groups that were self-pollinated and test-crossed to Pfister Hybrid 3000 and A632wx in summer 1992 were analyzed for oil percentage. Approximately 900 plants from the initial backcross populations to ASKC28 cytoplasm were discarded from the original 1,000 plants at harvest on the basis of vigor, disease and insect susceptibility, ear and kernel type, oil content and other characteristics. The mean TopCRoss™ grain oil content was fixed at 6.5 to 7.0 percent oil in the original selfs or sibs recovered from the backcross population to ASKC28 cytoplasm.

The ten families from each heterotic group expressing the highest oil percentage and best phenotype were used as parental material for a diallel mating series to produce three separate early testing populations: A-Reid, B-Lancaster and A-Reid×B-Lancaster to produce an early generation LP39 hybrid population for early generation tests to evaluate the success of recovery of favorable dominant oil gene linkage groups.

In the first cycle of the early generation test series of LP39A and LP39B, equal quantities of seed of each of the 45 diallel crosses within each heterotic population were bulked and the composite seed was used to plant isolation plots of approximately 20,000 plants which were random mated to establish the LP39A and LP39B synthetics as separate populations. The composite seed of the A-Reid×B-Lancaster diallel was also bulked to test LP39 in blends with male sterile hybrids for early generation yield trials for evaluation of the recovery of the favorable dominant oil gene linkage groups.

Additional crosses were also made to dent inbred testers, LH51 and LH132, by the A-Reid and B-Lancaster populations for general combining ability tests.

The ten populations of the early generation testing series within the Reid heterotic group (LH132 and NC282) and ten populations within the Lancaster heterotic group (LH51) were maintained by selfing. The ten Reid families were as follows: The $F_3$ from the backcross of AskC28 (LH132×AskC28) was selfed to produce $F_4$ generation designated LP39A1 and LP39A10; six populations of $F_2$ (AskC28 (LH132×AskC28)AskC28) were selfed to produce six $F_3$ populations designated LP39A2 through LP39A6 and LP39A9; and two populations of $F_3$ from the backcross of AskC28(NC282×AskC28) were selfed to produce LP39A7 and LP39A8.

The ten Lancaster families were as follows: Six $F_2$ populations of AskC28((LH51×AskC28)AskC28)S were selfed to produce $F_3$ populations designated LP39B1 and LP39B6 through LP39B10. Four populations of $F_3$ from the backcross of AskC28((LH51×AskC28)AskC28) were selfed to produce populations designated LP39B2 through LP39B5.

In addition, during the winter of 1992–93, an additional 100 ear-row families from each heterotic group having the highest oil percentage, earliest flowering dates and best agronomic phenotype were used as parental material for an inbreeding series for the final development of a late generation LP39. Concurrent with selection for improved phenotype in each of the succeeding inbreeding generations, test crosses to Pfister Hybrid 3000 were made and the resulting TopCross™ grain was analyzed for oil to identify normal grain type segregants with favorable dominant oil gene linkage groups.

Summer 1993: Inbreeding and Early Generation Tests

In summer of 1993, additional inbreeding of the Reid and Lancaster heterotic populations were carried out, producing $F_3$ and $F_4$ generations. In addition, intercrosses and single cross hybrid tests were conducted using the early generation LP39 testing series to obtain yield and genetic data for evaluating the success of recovery of favorable dominant oil genes. The LP39A and LP39B synthetic populations from the 45 entry bulk synthetic populations were also random mated in field isolation plots of approximately 20,000 plants.

Winter 1993–94: Inbreeding of Selected $F_4/F_5$ Populations and Production of Late Generation LP39 Testing Series The procedure for producing the LP39 synthetic hybrid with the A-Reid and B-Lancaster conversion populations for late generation testing and comparison to the early generation testing series was as follows: Approximately 100 plants from the Reid and Lancaster heterotic groups were advanced to $F_4$ or $F_5$ and test-crossed to tester Pfister Hybrid 3000 in summer of 1993 and were analyzed for oil percentage of TopCross™ grain. Approximately 90 families from the inbreeding series were discarded from the original 100 plants at harvest on the basis of vigor, disease and insect susceptibility, ear and kernel type, oil and other characters. The mean oil percentage was basically fixed in the parental material recovered from the backcross to ASKC28 cytoplasm while plant type was vastly improved in the $F_4$ or $F_5$ inbreeding series. However, two additional oil genes were recovered from oil linkage groups 9 and 11 in the selfing series (Table 18). By contrast, a major oil gene that contributes 18.2 percent of the oil variation and approximately two to three percent of the oil in TopCross™ grain was lost in both the early generation and late generation testing series in the 1992 generation when the normal starch grain types were advanced as parental material for the two breeding populations.

The ten families from each heterotic group expressing the highest oil percentage and best phenotype were used as parental material for a diallel mating series to produce three separate late generation LP39 populations: The A-Reid and B-Lancaster parental populations for LP39 and A-Reid×B-Lancaster to produce the final developed LP39 synthetic hybrid from the inbreeding series. For the final cycle from the late generation inbreeding series of LP39A and LP39B development, equal quantities of seed of each of the 45 diallel crosses within each heterotic population were bulked and the composite seed was used to plant isolation plots of approximately 20,000 plants which were random mated to establish the LP39A and LP39B synthetic as separate populations. The composite seed of the LP39A-Reid×LP39B-Lancaster diallel was also bulk tested in blends with male sterile hybrids to evaluate yield and the recovery of the favorable dominant oil gene linkage groups.

The ten populations of the late generation testing series within the Reid heterotic group (LH132 and NC282) and ten populations within the Lancaster heterotic group (LH51) were maintained by selfing. The ten Reid families were as follows: The three populations of $F_3$ from the backcross of ASKC28(LH132×ASKC28)-S were selfed to produce $F_4$ generational designated LP39A3, LP39A4 and LP39A5; two $F_3$ populations of ASKC28(LH132×ASKC28)-S were selfed to produce LP39A9 and LP39A10; one populations of $F_4$ ASKC28(LH132×ASKC28) was selfed to produce LP39A1; two populations of $F_4$ ASKC28(LH132×ASKC28) ASKC28 were selfed to produce LP39A2 and LP39A6; and two populations of $F_4$ASKC28(NC282×ASKC28) were selfed to produce LP39A7 and LP39A8. The ten Lancaster families were as follows: Six $F_3$ families of ASKC28 (LH51×ASKC28)ASKC28)-S were selfed to produce $F_4$ populations designated LP39B1, LP39B6 through LP39B10; and four $F_4$ families from the backcross of ASKC28(LH51×ASKC28)ASKC28 were selfed to produce populations designated LP39B2 through LP39B5.

In addition, during the winter of 1993–94, LP39ARM1 and LP39BRM1 were advanced by random mating in separate field isolations in South Florida, each isolation field consisting of approximately 20,000 plants from each heterotic population.

Summer 1994: $F_5$ and $F_6$ Generations

In summer of 1994, further inbreeding of the ten Reid and ten Lancaster families produced $F_5$ and $F_6$ generations. In addition, yield tests were continued for LP39 from the selfing series. Additional random mating for maintenance of LP39A and LP39B synthetic populations was continued.

Summary of LP39 Development

LP39 can be reproduced by planting synthetic populations LP39A and LP39B, allowing one synthetic to pollinate the other, and harvesting the resulting seed. Either synthetic parental population may be used as female parent or the male parent. Preferably, synthetic LP39B should be the female of the cross and synthetic LP39A should be the male of the cross because of the larger seed size grade-out resulting from the LP39B seed parent in hybrid synthetic production. Production planting of the male and female synthetics can be made at the same time due to the fact that male pollen is shed at the same time the female silks are receptive to the pollen.

LP39A and LP39B may be reproduced by conducting a series of crosses, selfings and backcrosses beginning with the crossing of LH132 and NC282 with ASKC28 (for LP39A) and the crossing of LH51 with ASKC28 (for LP39B). When produced according to the method disclosed herein, both LP39A and LP39B breed true, that is, produce an LP39 that is both reproducible and usable as a pollinator.

Performance Trials

In 1993 performance trials of the TopCross™ grain production system, LP39 was inter-planted with Pfister hybrid X571Sdms from the early generation series. This same procedure was repeated for the selfing series from $F_4$ or $F_5$ generation families and, based on performance of the lines per se in testcrosses, the 10 best families were advanced to reestablish a second cycle of LP39 which was evaluated in 1994. In each series, the plants selected for selfing were chosen on the basis of vigor and general desirability. The procedure of producing a hybrid synthetic involved growing the two heterotic groups (A-Reid and B-Lancaster populations) of intercrosses as separate progenies with maintenance of separate synthetic A and B populations for producing synthetic hybrid LP39 from random mated synthetic parents.

Each of the LP39A-Reid and LP39B-Lancaster synthetic populations used to produce LP39 in 1994 yield trials had been random mated for two generations. No major differences were observed in comparisons of $F_1$, RM1 and RM2 generations when compared in TopCross™ grain production tests.

3. Characteristics

LP39 has the following characteristics:

TABLE 2

LP39 SYNTHETIC HYBRID DESCRIPTION INFORMATION

| | | |
|---|---|---|
| | Type: | Dent/High Oil |
| | Region Best Adapted: | Most Northern Regions of Cornbelt |
| A. | Maturity | Zone 0 |
| | Synthetic Hybrid: | LP39 |
| | Heat Units from Emergence to Shed: | 1014.0 GDD |
| | Heat Units from Emergence to Silk: | 1014.0 GDD |
| | Heat Units from 50% Silk to 25% Kernel Moisture: | 1443.5 GDD |
| | Heat Units from Emergence to 25% Kernel Moisture: | 2457.5 GDD |
| | No. Reps.: | 8 |
| | Where Heat Units = [(Max. Temp. + Min. Temp.)*/2] − 50 *If maximum is greater than 86 degrees fahrenheit, then 86 is used and if minimum is less than 50, then 50 is used. Heat units accumulated daily and can not be less than 0. | |
| B. | Plant Characteristics: | |
| | Height (to tassel tip): | 219 cm |
| | Length of Top Ear Internode: | 15 cm |
| | Number of Ears per Stalk: | 1–2, slight two-ear tendency |
| | Ear Height (to base of top ear): | 63 cm |
| | Number of Tillers: | None |
| | Cytoplasm Type: | Normal |
| | Brace Root Color: | Dark Green |
| | Number of Brace Root Nodes: | 1 |
| | Number of Brace Roots: | 12 |
| C. | Leaf: | |
| | Color: | Green |
| | Stalk Color: | Green |
| | Angle from Stalk: | 53 Degrees |
| | Marginal Waves (number): | 2–3, few |
| | Number of Leaves (mature plants): | 11 |
| | Sheath Pubescence: | Smooth, pubescence absent |
| | Longitudinal Creases: | Absent |
| | Length (Ear node leaf): | 68 cm |
| | Width (widest point, ear node leaf): | 8 cm |
| | Coleoptile Sheath Color: | Purple |
| D. | Tassel: | |
| | Number Lateral Branches: | 12 |
| | Branch Angle from central spike: | 57 degrees |
| | Length (from flag leaf): | 48 cm |
| | Pollen Shed: | 5.146 gm/plant: medium quantity of pollen produced from each plant for a duration of 18 days for the LP39 synthetic population |
| | Peduncle Length (flag leaf to basal branches): | 32 cm |
| | Anther Color: | Yellow; was segregating for purple and yellow anther color but fixed for yellow. |

TABLE 2-continued

LP39 SYNTHETIC HYBRID DESCRIPTION INFORMATION

| | | |
|---|---|---|
| | Glume Color: | Green; was segregating for green/red stripe |
| E. | Ear (Husked Ear Data Except When Stated Otherwise): | |
| | Length: | 21 cm |
| | Weight (dried to 15.5 percent grain moisture): | 188 gm |
| | Mid-point Diameter: | 5 cm |
| | Silk Color (at silking): | Pale green |
| | Husk Extension (Harvest stage): | Short, 0.6 cm (ear tip occasionally exposed) |
| | Husk Leaf (number): | 7 |
| | Husk Leaf Length: | 9 cm |
| | Number of Husks: | 13 |
| | Taper of Ear: | Average taper |
| | Position at Dry Husk Stage: | Upright |
| | Kernel Rows: | 18; Distinct, straight, segregating 14 to 20 |
| | Husk Color (fresh): | Light green |
| | Husk Color (dry): | Buff |
| | Shank Length: | 18 cm long |
| | Shank (No. of internodes): | 10 |
| | Drying Time (unhusked ear): | Average |
| | Husk Length: | 23 cm |
| | Husk Width: | 15 cm |
| | Husk Area: | 340 cm2 |
| F. | Kernel (dried, size from ear mid-point): | |
| | Length: | 11 mm |
| | Width: | 7 mm |
| | Thickness: | 4 mm |
| | Shape Grade (% rounds): | 35% (±3%) based on parent test |
| | Pericarp Color: | Colorless |
| | Aleurone Color: | Homozygous; yellow |
| | Cap Color: | Yellow |
| | Endosperm Color: | Yellow |
| | Endosperm Starch Type: | Normal starch |
| | Gm Wt/100 Seeds (unsized): | 22 gm |
| | Test Weight: | 60 lbs./bu. |
| | Percent Oil: | 13.57 Percent |
| | Percent Protein: | 12.15 Percent |
| | Percent Starch: | 59 Percent |
| G. | Cob (dried, size from ear mid-point): | |
| | Diameter at mid-point: | 26 mm |
| | Strength: | Strong |
| | Color: | Red, segregating for white and red cob color but was heterozygous for red. |
| H. | Diseases: | |
| | Northern Leaf Blight: | Intermediate |
| | Goo's Bacterial Blight: | Intermediate |
| | Southern Corn Leaf Blight: | Susceptible |
| | Heat Smut: | Susceptible |
| | Common Smut: | Resistant |
| | Stewart's Bacterial Wilt: | Intermediate |
| | Corn Lethal Necrosis: | Susceptible |
| | Northern Leaf Spot: | Intermediate |
| | Common Northern Rust: | Intermediate |
| | Southern Rust: | Susceptible |
| | Eye Spot: | Intermediate |
| | Gray Leaf Spot: | Susceptible |
| | Fusarium Ear Rot: | Resistant |
| | Fusarium Stalk Rot: | Intermediate |
| | Diplodia Ear Rot: | Susceptible |
| | Diplodia Stalk Rot: | Intermediate |
| | MDMV: | Susceptible |
| | Stunt: | Susceptible |
| | Stay Green: | Intermediate |
| I. | Insects: | |
| | European Corn Borer: | Susceptible |
| J. | Variety most closely resembling: | |

| Character | Synthetic and/or Hybrid, Inbred |
|---|---|
| Maturity | W117, X571 |
| Plant Type | ASKC28, UHO, ASKC20 |
| Ear Type | ASKC28, UHO, ASKC20 |
| Kernel Type | UHO, ASKC20 |
| Useage | ASKC28, UHO, ASKC20 |

Synthetic corn hybrid LP39 most closely resembles maize synthetics ASKC28, ASKC20 and UHO in characteristics of plant type, ear type, kernel type and usage, but LP39 is considerably earlier in maturity and expresses higher grain test weight with normal grain and dent phenotype.

LP39 is adapted over a wide area of the northern corn belt and can be used advantageously in seed blends with male sterile hybrids from approximately 96–105 relative maturity based on the Minnesota Relative Maturity Rating System for harvest moisture of the grain. LP39 cold test vigor was excellent in laboratory tests, exhibiting 92% emergence compared to 90% emergence for ASKC20, 92% emergence for UHOC3, and 83% emergence for ASKC28 (LSD=8.5%; C.V.=5.6% at 0.05 and Stand. Dev.=4.4). Kernel size-out is also very good for LP39, with approximately 59 percent of the kernels falling in the medium flat category.

Although LP39's primary use would be as a pollinator in the TopCross™ grain production system with blends of early maturing corn hybrid male sterile grain parents, it is also an acceptable male to be crossed to later maturing full season high oil pollinators to develop medium maturity pollinators for expanding the use of its genetics to fuller season maturity grain parents.

Pollen production is good, with LP39 producing 5.2 grams of pollen per plant in replicated trials in 1994 (Table 15). Under extreme heat and drought stress, LP39 may top fire and have some tassel blasting (necrosis of top leaves and tassel, respectively). It sheds pollen for approximately eighteen days and should be planted in 8 to 20 percent blends to ensure adequate pollen in commercial production of TopCross™ grain where it is used as a male pollinator (Table 16).

LP39 has shown uniformity and stability within the limits of environmental influence for all traits as described in Table 2. LP39 has expressed segregation for red and white cob color because of the genetic difference of LP39A and LP39B synthetic parent populations. LP39 is a synthetic hybrid that has been maintained by hand and cross pollination in isolated fields with continued observation of high oil for uniformity of dominant high oil genetics. Although segregating for cob color, glume color and plant height in test crosses, LP39 synthetic has expressed high oil consistently across different environments.

LP39 is an early flowering synthetic hybrid, broadly adapted to the corn growing areas of the Northern United States and Southern Canada. LP39 has high oil and excellent cold soil seedling vigor that conditions low grain moisture in the grain of the male sterile hybrid grain parent.

4. Benefits of LP39 as a Pollinator

In field tests of the TopCross™ grain production system using LP39 as the pollinator and a male sterile hybrid grain parent, plants of both varieties were allowed to grow unmolested to maturity. Both varieties were allowed to continue to grow and natural cross-pollination occurred by the action of wind as is normal in most grasses, including corn (i.e., excluding wheat). Of course, only pollen from the male parent synthetic hybrid, LP39, was available for pollination of the male sterile hybrid grain parent; the tassels, or pollen bearing flowering parts, of the grain parent having been rendered sterile by genetic/cytoplasmic mechanisms.

The fields where high oil TopCross™ grain was produced were well isolated from other corn fields to prevent any accidental contamination with ambient pollen. Such isolation techniques may be accomplished by timed delay with other hybrid corn production fields or by using a space distance pattern of more than 70 m from normal corn, well known to those skilled in the art of the seed corn industry.

Both varieties comprising the corn seed blend were allowed to continue to grow and be harvested. The ears harvested from the male sterile grain parent expressed higher grain yield potential of the elite male sterile grain parent and high oil, protein and grain density from the pollen parent. The male parent variety ears can also be harvested for high oil corn use along with the grain of male sterile grain parent.

Because the same oil source (i.e. ASKC28) was used in the development of the A-Reid and B-Lancaster populations, only modest heterotic effects for yield were expressed in LP39. The low grain yields expected from synthetic hybrid LP39 pollinator dictated the need for a low percent of 8 to 20 percent pollinator seed blend ratio to grain parent seed ratio so as to recover the grain quality traits of the pollinator while producing sufficient pollen to maintain the higher yield potential of the elite male sterile grain parent hybrid.

LP39 induces superior grain quality characteristics to TopCross™ grain of the male sterile hybrid grain parent as a result of being pollinated by LP39. That is to say, the grain quality traits and high oil characteristics of LP39 were transferred to the grain of the male sterile grain parent.

EXAMPLES OF LP39'S USEFULNESS AS A POLLINATOR

In the examples that follow, the characteristics of TopCross™ grain produced using LP39 as a pollinator are given.

Example I

Strip Test Grain Yields

Comparison yield data was collected from strip tests that were grown by expert professional research affiliate cooperators. Each seed blend was grown in 91 m long strips of a minimum of 48 rows in field isolation and were sown in strips of 12, 24, 36, etc. rows for each hybrid blend, depending on the number of different male sterile grain parent hybrids that were compared with a common pollinator. The data was collected from strip tests that had the fertile check hybrids sown in the same field at a distance of more than 70 m from the seed blends. At harvest, the grain was harvested from a measured area and weighed. The moisture percentage was determined to compute yield and bushels per acre was adjusted to 15.5 percent moisture. Each replication or "rep" represents a distinct field plot.

The primary grain parent hybrids utilized in strip test trials are in the same maturity as the hybrid pollinator LP39 while additional grain parent hybrids were included in related trials to illustrate modifications that may be practiced within the scope of this invention. All grain parent hybrids presented for purposes of illustration and examples were produced and marketed and are readily available from Pfister Hybrid Corn Company of El Paso, Ill.

The seed blend consisted of an eight percent seed admixture of fertile LP39 hybrid pollinator seed that was dyed green to 92 percent cytoplasmic male sterile grain parent hybrid seed that was dyed red to facilitate monitoring of seed blending in a rotating drum for smaller quantities of seed admixtures. For larger quantities of blends, the pollinator seed was transported across a vibrating conveyor into a collecting funnel that had a premeasured quantity of male sterile grain parent hybrid seed simultaneously conveyed at a predetermined flow rate for eight percent blends from an elevated holding bin into the collecting funnel. The grain parent seed was combined with the pollinator seed as each flowed into the collecting funnel. The blended seed was then dispensed into a seed bag filled to a predetermined weight of blended seed, depending on its intended use and grade size.

It was essential to blend similar grade sizes of pollinator seed with male sterile grain parent seed to establish a uniform seed admixture that could be accurately sown by corn planters and less likely to gravity separate while being transported to the field in the seed bag or separated in the planter box. Also, it was imperative that smaller and larger seed sizes of pollinator seed that were produced be discarded prior to blending because of germination problems, off-types and poor seed match to grade size of grain parent.

Comparison strip testing was done between the seed blends and their corresponding fertile hybrids. Comparison strip testing was also done between Pfister hybrids X529, X571, X577, X586, 2020, 3000 and 3034 that were included in the same field experiment of seed blends with TC Blend™ seed and compared to the fertile hybrids.

Traits obtained from the strip test data, in addition to those defined previously, are as follows:

Yield is expressed bushels per acre for both the grain produced by the pollination of the male sterile hybrid by LP39 and for the fertile hybrid. Yield of grain from the male sterile/LP39 seed blend is also expressed as a percent of the yield from the fertile grain parent yield.

Grain moisture (for grain produced from the seed blend and from the fertile grain parent) is expressed as a percentage of total kernel weight. Relative grain moisture was determined by distillation on a Brown-Duvel moisture tester manufactured by the Seed Trade Reporting Bureau, Chicago, Ill. Electronic moisture testers were calibrated against the moisture determinations of the Brown-Duvel moisture tester in field harvest tests.

Oil content is expressed in the tables as the percentage of oil in the grain at harvest and was determined by NIR on a dry matter basis (0% moisture). Similarly, protein is expressed as the percentage of protein in the grain on a dry matter basis as determined by NIR.

Grain density was determined as weight of grain per ml of seed based on water displacement tests while test weight was determined from weight of grain in pounds and was presented as pounds per bushel.

In first year trials, the LP39 hybrid pollinator was tested in hybrid TC Blend™ seed blends in strip tests at El Paso, Ill. and Janesville, Wis. These results are provided in Table 3 below:

TABLE 3

1993 LP39 Strip Test Results

| Hybrid | Yield (Bu/A.) | Yield % GP | Erect % | Grain Moisture % | Test Wt. Lbs/bu. | 50 K wt gm | Oil % | Flowering GDD Tassel | Silk |
|---|---|---|---|---|---|---|---|---|---|
| El Paso, Illinois | | | | | | | | | |
| LP39 + Pfister hybrid X571Sdms | 117.2 | 89 | 88 | 15.0 | 53.9 | 13.4 | 6.49 | 1147.5 | 1166.0 |
| Pfister Hybrid X571 | 131.8 | — | 92 | 18.0 | 55.0 | 14.3 | 4.66 | 1166.0 | 1166.0 |
| LP39 + Pfister Hybrid 3000Sdms | 121.4 | 102 | 74 | 18.7 | 56.3 | 13.7 | 6.31 | 1147.5 | 1263.0 |
| Pfiser Hybrid 3000 | 119.3 | — | 94 | 20.1 | 54.6 | 14.9 | 4.38 | 1263.0 | 1263.0 |
| Janesville, Wisconsin | | | | | | | | | |
| LP39 + Pfister Hybrid X571Sdms | 137.0 | 93 | — | 19.5 | 56.0 | — | 6.40 | — | — |
| Pfister Hybrid X571 | 146.3 | — | — | 22.5 | 56.0 | — | 4.30 | — | — |

At blends of 8–9 percent of pollinator and 91–92 percent male sterile grain parent, little loss in total grain yield was observed in total grain yield of the male sterile grain parent. For example, the yield achieved from a blend of 8% LP39 and 92% Sdms-cytoplasmic male sterile grain parent hybrid Pfister X571-Sdms (117.2 Bu/A) was only slightly less than the yield obtained from a grow out of Pfister Hybrid X571 (131.8 Bu/A). Yields of seed blends containing LP39 at the El Paso location were 89 and 102 percent of yield of the fertile grain parent checks, Pfister X571 and Pfister 3000, respectively, while at the Janesville location, TopCross™ grain yields were 93 percent of the grain parent check X571.

The LP39 intercrosses and single crosses were also tested at Clinton, Pesotum and El Paso, Ill.; Peru, Ind. and Brookings, S.D. These results are provided below:

In the experimental intercrosses and single cross yield test comparisons, LP39 single crosses (i.e., dent inbred×LP39) yielded 88 percent compared to the yield obtained from a grow out of Pfister X571 (121.9 Bu/A compared to 138.1 Bu/A), while LP39A×LP39B intercrosses yielded 33 percent compared to the yield obtained from a grow out of Pfister X571 (48.9 Bu/A compared to 148.1 Bu/A).

In second year yield trials, LP39 was evaluated in seed blends with seven male sterile grain parent hybrids at Corn Research Stations in Evansville, Wis.; Paulina, Humbolt and Waterloo, Iowa; Cannon Falls, Minn. and Geneseo, Ill. These results are provided below:

TABLE 4

1993 Hybrid Comparisons of LP39 Single Crosses, LP39AxLP39B Intercrosses, and PFister Hybrid X571.

| Hybrid | Yield Bu/A. | Erect % | Dropped Ears | Root Lodged % | Grain Moisture % | No. Reps | Height (cm) Plant | Ear | GDD to Tassel | Silk | TopCross Oil % Hyb. 3000 |
|---|---|---|---|---|---|---|---|---|---|---|---|
| LP39 Single Crosses | 121.9 | 82.9 | 0.50 | 0.0 | 28.94 | 102 | 275.1 | 98.6 | 1160.0 | 1218.5 | 5.97 |
| Pfister X571 | 138.1 | 98.4 | 0.00 | 0.0 | 21.82 | 6 | 259.1 | 100.7 | 1190.5 | 1166.0 | — |
| LSD | 34.4 | 20.7 | 1.27 | 1.0 | 3.96 | 108 | — | | — | | — |
| Stand. Dev. | 8.2 | 9.4 | 0.44 | 0.0 | 2.92 | 108 | — | | — | | — |
| C.V. % (0.05) | 19.0 | 15.1 | 162.99 | 650.0 | 6.09 | 108 | — | | — | | — |
| LP39AxLP39B Intercrosses | 48.9 | 79.5 | 1.20 | 1.0 | 20.32 | 297 | 257.8 | 73.4 | 1147.5 | 1166.0 | 6.31 |
| Pfister X571 | 148.1 | 99.1 | 0.35 | 0.0 | 15.79 | 9 | 259.1 | 106.7 | 1190.5 | 1166.0 | — |
| LSD | 32.9 | 57.6 | 3.38 | 4.0 | 15.10 | 306 | — | | — | | — |
| Stand. Dev. | 17.6 | 24.0 | 1.04 | 2.0 | 5.45 | 306 | — | | — | | — |
| C.V. % (0.05) | 14.4 | 10.1 | 95.47 | 110.0 | 6.78 | 306 | — | | — | | — |

1. Stations Tested: Clinton, Pesotum and EPaso, Illinois and Peru, Indiana.
2. Stations Tested: El Paso, Illinois and Brookings, South Dakota.
3. Average of LH82xLP39A and LH132xLP:B Single Crosses (18 entries).
4. Average of LP39AxLP39B diallel intercrosses. The intercrosses mixed together in a separate bulk constituted the early generation LP39 for the early generation testing series.

TABLE 5

Average hybrid yield, grain moisture, oil, protein and grain density by TopCross pollinator performance comparing LP39 and LP39(LG) within a location when TopCrossed to a sterile hybrid grain parent compared to the fertile grain parent self pollinated in the same experimental location which consisted of fertile control in one isolation and sterile hybrid TopCross blend in another isolation.

| | Grain Yield-Bu/A. | | | Moisture | | | Oil | | | Protein | | | Density (gm/ml) | | |
|---|---|---|---|---|---|---|---|---|---|---|---|---|---|---|---|
| | Top-Cross | % of GP | Hybrid* Self | Top-Cross | % of GP | Hybrid Self | Top-Cross* | % of GP | Hybrid Self | Top-Cross* | % of GP | Hybrid Self | Top-Cross* | % of GP | Hybrid Self |
| LP39 TopCross Pollinator | | | | | | | | | | | | | | | |
| Pfister Hybrid X571-Sdms | | | | | | | | | | | | | | | |
| Evansville, Wis. | 166.5 | 90 | 184.7 | 18.6 | 100 | 18.5 | 6.9 | 156 | 4.4 | 9.2 | 103 | 8.9 | 1.25 | 96 | 1.30 |
| Paulina, Ia. | 164.0 | 92 | 179.0 | 19.7 | 104 | 18.8 | 7.7 | 154 | 5.0 | 9.6 | 93 | 10.3 | 1.25 | 104 | 1.20 |
| Cannon Falls, MN | 178.0 | 95 | 188.0 | 16.9 | 90 | 18.7 | 6.9 | 150 | 4.6 | 9.2 | 98 | 9.3 | 1.26 | 100 | 1.26 |
| Pfister Hybrid X586-Sdms | | | | | | | | | | | | | | | |
| Evansville, Wis. | 184.9 | 91 | 202.7 | 19.5 | 104 | 18.7 | 6.9 | 160 | 4.3 | 9.4 | 111 | 8.5 | 1.29 | 96 | 1.34 |
| Cannon Falls, MN | 184.0 | 94 | 196.0 | 18.8 | 96 | 19.5 | 7.1 | 169 | 4.2 | 9.3 | 112 | 8.3 | 1.28 | 99 | 1.29 |
| Pfister Hybrid 2020-Sdms | | | | | | | | | | | | | | | |
| I Evansville, Wis. | 193.0 | 91 | 211.4 | 20.0 | 87 | 23.0 | 6.4 | 160 | 4.0 | 8.2 | 100 | 8.2 | 1.25 | 98 | 1.28 |
| II Evansville, Wis. | 191.7 | 91 | 211.4 | 19.0 | 83 | 23.0 | 7.0 | 175 | 4.0 | 9.0 | 111 | 8.1 | 1.31 | 102 | 1.28 |
| Geneseo, Ill. | 221.7 | 100 | 222.0 | 15.5 | 100 | 15.5 | 7.5 | 163 | 4.6 | 8.0 | 100 | 8.0 | 1.21 | 99 | 1.22 |
| Humbolt, Ia. | 166.3 | 90 | 184.6 | 17.4 | 98 | 17.7 | 6.7 | 136 | 4.9 | 8.9 | 101 | 8.8 | 1.24 | 107 | 1.16 |
| Waterloo, Ia. | 161.7 | 96 | 167.7 | 20.9 | 95 | 22.1 | 6.7 | 176 | 3.8 | 6.9 | 87 | 7.9 | 1.19 | 103 | 1.16 |
| I Cannon Falls, MN | 199.0 | 100 | 200.0 | 20.9 | 99 | 21.2 | 5.7 | 158 | 3.6 | 8.1 | 99 | 8.2 | 1.17 | 101 | 1.15 |
| II Cannon Falls, MN | 184.0 | 94 | 196.0 | 18.8 | 96 | 19.5 | 7.1 | 182 | 3.9 | 8.4 | 106 | 7.9 | 1.22 | 100 | 1.21 |
| Pfister Hybrid X529-Sdms | | | | | | | | | | | | | | | |
| I Evansville, Wis. | 187.9 | 90 | 208.1 | 20.0 | 87 | 23.0 | 6.3 | 150 | 4.2 | 9.1 | 107 | 8.5 | 1.22 | 92 | 1.32 |
| II Evansville, Wis. | 182.2 | 95 | 192.0 | 24.4 | 108 | 22.5 | 7.4 | 176 | 4.2 | 9.0 | 107 | 8.4 | 1.28 | 99 | 1.29 |
| Pfister Hybrid 3000-Sdms | | | | | | | | | | | | | | | |
| Evansville, Wis. | 194.2 | 99 | 195.2 | 24.4 | 106 | 23.0 | 7.3 | 173 | 4.2 | 9.8 | 115 | 8.5 | 1.27 | 98 | 1.30 |
| Geneseo, Ill. | 223.1 | 116 | 192.7 | 16.9 | 100 | 16.9 | 8.1 | 169 | 4.8 | 8.9 | 96 | 9.3 | 1.21 | 102 | 1.19 |
| Humbolt, Ia. | 172.3 | 91 | 189.0 | 19.9 | 101 | 19.8 | 7.9 | 161 | 4.9 | 9.8 | 105 | 9.3 | 1.11 | 97 | 1.14 |
| Waterloo, Ia. | 166.6 | 101 | 165.2 | 24.5 | 94 | 26.0 | 6.5 | 158 | 4.1 | 8.8 | 110 | 8.0 | 1.18 | 98 | 1.20 |
| Pfister Hybrid 3034-Sdms | | | | | | | | | | | | | | | |
| Evansville, Wis. | 189.7 | 93 | 203.7 | 21.1 | 96 | 22.0 | 6.4 | 146 | 4.4 | 8.2 | 93 | 8.8 | 1.31 | 99 | 1.32 |
| Pfister Hybrid X577-Sdms | | | | | | | | | | | | | | | |
| Evansville, Wis. | 182.2 | 95 | 191.3 | 24.4 | 103 | 22.5 | 7.4 | 132 | 5.6 | 9.6 | 103 | 9.3 | 1.28 | 99 | 1.29 |
| Geneseo, Ill. | 207.9 | 98 | 212.9 | 16.9 | 98 | 17.2 | 8.2 | 161 | 5.1 | 9.6 | 100 | 9.6 | 1.21 | 102 | 1.18 |
| Humbolt, Ia. | 148.4 | 76 | 196.2 | 20.9 | 105 | 19.9 | 7.3 | 143 | 5.1 | 10.6 | 117 | 9.1 | 1.11 | 96 | 1.15 |
| Waterloo, Ia. | 151.4 | 94 | 161.8 | 26.1 | 91 | 28.4 | 6.3 | 146 | 4.3 | 9.0 | 112 | 8.0 | 1.18 | 98 | 1.20 |
| Mean | 182.6 | 94 | 193.4 | 20.2 | 97 | 20.8 | 7.0 | 159 | 4.4 | 9.0 | 103 | 8.7 | 1.23 | 99 | 1.24 |
| LP39(LG) Topcross Pollinator | | | | | | | | | | | | | | | |
| Pfister Hybrid X571-Sdms | | | | | | | | | | | | | | | |
| Evansville, Wis. | 165.2 | 89 | 184.7 | 18.8 | 101 | 18.5 | 6.9 | 156 | 4.4 | 9.4 | 106 | 8.8 | 1.26 | 104 | 1.21 |
| Pfister Hybrid X586-Sdms | | | | | | | | | | | | | | | |
| Evansville, Wis. | 183.2 | 90 | 202.4 | 19.5 | 104 | 18.7 | 7.3 | 170 | 4.3 | 10.1 | 120 | 8.4 | 1.28 | 95 | 1.34 |
| Pfister Hybrid 2020-Sdms | | | | | | | | | | | | | | | |
| Evansville, Wis. | 201.4 | 95 | 211.4 | 18.0 | 78 | 23.0 | 7.0 | 175 | 4.0 | 8.7 | 106 | 8.2 | 1.32 | 103 | 1.28 |
| Pfister Hybrid X529-Sdms | | | | | | | | | | | | | | | |
| Evansville, Wis. | 186.0 | 89 | 208.1 | 23.5 | 102 | 23.0 | 6.6 | 157 | 4.2 | 8.9 | 106 | 8.4 | 1.25 | 95 | 1.32 |
| Pfister Hybrid | | | | | | | | | | | | | | | |

TABLE 5-continued

Average hybrid yield, grain moisture, oil, protein and grain density by TopCross pollinator performance comparing LP39 and LP39(LG) within a location when TopCrossed to a sterile hybrid grain parent compared to the fertile grain parent self pollinated in the same experimental location which consisted of fertile control in one isolation and sterile hybrid TopCross blend in another isolation.

| | Grain Yield-Bu/A. | | | Moisture | | | Oil | | | Protein | | | Density (gm/ml) | | |
|---|---|---|---|---|---|---|---|---|---|---|---|---|---|---|---|
| | Top-Cross | % of GP | Hybrid* Self | Top-Cross | % of GP | Hybrid Self | Top-Cross* | % of GP | Hybrid Self | Top-Cross* | % of GP | Hybrid Self | Top-Cross* | % of GP | Hybrid Self |
| 3034-Sdms | | | | | | | | | | | | | | | |
| Evansville, Wis. | 181.4 | 89 | 203.7 | 22.0 | 114 | 22.0 | 6.4 | 146 | 4.4 | 8.6 | 97 | 8.8 | 1.30 | 99 | 1.32 |
| Mean | 183.4 | 90 | 202.7 | 21.0 | 100 | 21.0 | 6.8 | 158 | 4.3 | 9.1 | 107 | 8.5 | 1.28 | 99 | 1.29 |
| T 0.05 | | 5.07* | | | 1.25 | | | 5.65* | | | 3.04* | | | 0.91 | |

*Population means were significantly different at 0.05 in paired t-test comparisons for grain yield, percent oil and percent grain protein while there was no significant difference for percent grain moisture and grain density. All TopCross blends were compared at 8 percent TopCross pollinator blends to sterile hybrid grain parent seed ratios.

In the second year yield trials summarized above, the yield from the LP39 seed blends averaged 94 percent of the yield from the fertile hybrid grain parents in 23 strip tests. The yield from late generation LP39 seed blends averaged 90 percent of the yield from the fertile grain parent checks.

Example II

Oil Content of TopCross™ Grain

Comparisons of the oil content of TopCross™ grain were made against the oil content of grain from fertile hybrids in strip tests and from additional studies of a more preliminary nature with 22 male sterile hybrid grain parents pollinated by LP39. In other studies, oil content of grain from late generation LP39 seed blends was compared in separate yield strip tests and in additional studies with the oil content of grain from 31 fertile hybrids. The results of these comparisons are presented in Tables 3, 4 and 5, and in Tables 6, 7, 8, 9, 10, 11 and 12 below:

TABLE 6

Average percent oil and protein of grain from the same experiment in comparisons of 22 fertile hybrid grain parents compared to sterile version of same hybrid pollinated by LP39 (1993 Data).

| | | Percent Oil | | Percent Protein | | |
|---|---|---|---|---|---|---|
| Hybrid Pfister | GDD Silk | Self Pollinated | LP39 Topcross | Self Pollinated | LP39 Topcross | No. Reps. |
| X571 | 1141 | 4.47 | 7.57 | 11.2 | 12.4 | 12 |
| X529 | 1161 | 4.45 | 7.69 | 9.7 | 12.4 | 10 |
| 2020 | 1171 | 4.38 | 7.98 | 7.9 | 12.1 | 11 |
| 3000 | 1192 | 5.34 | 8.02 | 12.2 | 13.6 | 11 |
| 2277 | 1199 | 4.11 | 7.72 | 10.2 | 13.1 | 9 |
| X528 | 1209 | 4.78 | 8.28 | 10.4 | 11.9 | 10 |
| 2375 | 1217 | 4.64 | 6.96 | 12.4 | 14.8 | 10 |
| 2388 | 1227 | 4.61 | 7.55 | 12.3 | 12.9 | 11 |
| 3333 | 1237 | 4.97 | 8.21 | 12.4 | 14.1 | 13 |
| X577 | 1242 | 4.52 | 8.23 | 12.1 | 13.6 | 9 |
| X570 | 1252 | 4.20 | 6.99 | 12.6 | 14.1 | 10 |
| X519 | 1262 | 4.69 | 7.93 | 13.0 | 13.1 | 10 |

TABLE 6-continued

Average percent oil and protein of grain from the same experiment in comparisons of 22 fertile hybrid grain parents compared to sterile version of same hybrid pollinated by LP39 (1993 Data).

| | | Percent Oil | | Percent Protein | | |
|---|---|---|---|---|---|---|
| Hybrid Pfister | GDD Silk | Self Pollinated | LP39 Topcross | Self Pollinated | LP39 Topcross | No. Reps. |
| 2725 | 1270 | 4.80 | 7.26 | 12.1 | 14.4 | 11 |
| 3339 | 1275 | 4.48 | 7.23 | 11.8 | 13.8 | 7 |
| X524 | 1280 | 4.83 | 7.12 | 11.8 | 12.1 | 9 |
| X515 | 1283 | 4.55 | 7.40 | 12.5 | 13.4 | 5 |
| X518 | 1286 | 4.68 | 6.93 | 11.3 | 13.8 | 9 |
| X464 | 1290 | 4.97 | 7.80 | 12.4 | 13.8 | 10 |
| X530 | 1294 | 4.49 | 7.50 | 12.4 | 14.7 | 8 |
| 2417 | 1295 | 4.61 | 7.41 | 11.5 | 13.9 | 3 |
| X465 | 1300 | 4.72 | 6.40 | 12.1 | 14.2 | 2 |
| 3434 | 1314 | 4.82 | 7.37 | 12.4 | 14.4 | 6 |
| LP39-Sib | 1168 | 11.72 | — | 12.1 | — | 36 |
| Mean of each column | | 4.95 | 7.53 | 11.69 | 13.48 | |
| *LSD (0.05) | | 0.13 | 0.13 | 0.14 | 0.14 | |
| Stand. Dev.. | | 1.50 | 0.48 | 1.16 | 0.87 | |
| C.V. % (0.05) | | 1.64 | 1.05 | 0.72 | 0.63 | |
| Mean of Group | | 6.21 | | 12.56 | | |
| LSD (0.05) | | 0.13 | | 0.13 | | |
| Stand. Dev. | | 1.71 | | 1.36 | | |
| C.V. % (0.05) | | 1.28 | | 0.66 | | |

*Waller-Duncan's Bayesian K-ratio t-test.

TABLE 7

Grain composition information from five grain parent hybrids pollinated by LP39(LG) compared to self pollinated hybrids (1994).**

| Grain Characteristics* | Pollen: | Pfister X571 Self | Pfister X571Sdms LP39 | Pfister X529 Self | Pfister X529Sdms LP39 | Pfister X586 Self | Pfister X586Sdms LP39 | Pfister 2020 Self | Pfister 2020Sdms LP39 | Pfister 3034 Self | Pfister 3034Sdms LP39 |
|---|---|---|---|---|---|---|---|---|---|---|---|
| Test Wt. (lbs/Bu.) | | 60.68 | 60.84 | 59.06 | 63.08 | 60.58 | 61.52 | 59.04 | 58.54 | 60.32 | 61.24 |
| 100K Wt. (gms) | | 36.30 | 34.30 | 34.86 | 36.00 | 35.17 | 29.43 | 32.40 | 32.61 | 36.80 | 32.00 |
| Density (gm/ml) | | 1.20 | 1.22 | 1.24 | 1.25 | 1.24 | 1.24 | 1.23 | 1.24 | 1.25 | 1.27 |
| Oil (%) | | 4.39 | 8.05 | 3.96 | 8.27 | 4.12 | 9.42 | 3.84 | 7.93 | 3.63 | 8.33 |
| Protein (%) | | 11.11 | 13.00 | 11.50 | 13.83 | 13.35 | 15.50 | 10.41 | 11.88 | 11.11 | 12.18 |
| Starch (%) | | 71.00 | 64.00 | 70.00 | 63.00 | 70.00 | 61.00 | 71.00 | 65.00 | 70.00 | 64.00 |
| Cysteine (%) | | 0.26 | 0.29 | 0.26 | 0.31 | 0.28 | 0.33 | 0.25 | 0.27 | 0.23 | 0.23 |
| Aspartate (%) | | 0.77 | 0.78 | 0.78 | 0.90 | 0.89 | 1.01 | 0.72 | 0.76 | 0.74 | 0.66 |
| Methionine (%) | | 0.25 | 0.29 | 0.25 | 0.31 | 0.29 | 0.35 | 0.23 | 0.27 | 0.26 | 0.20 |
| Threonine (%) | | 0.41 | 0.44 | 0.44 | 0.49 | 0.46 | 0.55 | 0.39 | 0.43 | 0.43 | 0.36 |
| Serine (%) | | 0.59 | 0.62 | 0.63 | 0.71 | 0.69 | 0.82 | 0.54 | 0.59 | 0.61 | 0.49 |
| Glutamate (%) | | 2.29 | 2.42 | 2.38 | 2.81 | 2.78 | 3.31 | 2.06 | 2.24 | 2.26 | 1.92 |
| Glycine (%) | | 0.42 | 0.45 | 0.43 | 0.49 | 0.45 | 0.52 | 0.40 | 0.46 | 0.41 | 0.37 |
| Alanine (%) | | 0.92 | 0.92 | 0.95 | 1.07 | 1.10 | 1.27 | 0.83 | 0.87 | 0.90 | 0.76 |
| Valine (%) | | 0.55 | 0.57 | 0.57 | 0.66 | 0.63 | 0.74 | 0.50 | 0.56 | 0.53 | 0.47 |
| Isoleucine (%) | | 0.42 | 0.44 | 0.44 | 0.51 | 0.50 | 0.60 | 0.39 | 0.42 | 0.42 | 0.36 |
| Leucine (%) | | 1.64 | 1.61 | 1.65 | 1.88 | 2.01 | 2.28 | 1.48 | 1.48 | 1.58 | 1.30 |
| Phenylalanine (%) | | 0.57 | 0.61 | 0.62 | 0.67 | 0.68 | 0.82 | 0.53 | 0.56 | 0.59 | 0.50 |
| Lysine (%) | | 0.36 | 0.34 | 0.34 | 0.38 | 0.37 | 0.38 | 0.34 | 0.35 | 0.32 | 0.30 |
| Histidine (%) | | 0.36 | 0.35 | 0.38 | 0.41 | 0.39 | 0.42 | 0.35 | 0.36 | 0.34 | 0.34 |
| Arginine (%) | | 0.56 | 0.58 | 0.58 | 0.65 | 0.58 | 0.68 | 0.51 | 0.58 | 0.53 | 0.47 |
| Tryptohan (%) | | 0.096 | 0.095 | 0.088 | 0.101 | 0.093 | 0.105 | 0.080 | 0.092 | 0.081 | 0.098 |
| Tyrosine (%) | | 0.50 | 0.053 | 0.58 | 0.63 | 0.59 | 0.72 | 0.47 | 0.51 | 0.56 | 0.60 |

*Averages expressed as mean values from the same experiment for comparison of the fertile grain parents compared to the TopCrossed grain of the sterile hybrids TopCrossed by pollinator LP39.
**AGP Limited (P.O. Box 117, Courtland, Minn. 56021) conducted the wet chemistry grain composition analysis on a dry matt tter basis determining protein content by combustion nitrogen analysis and oil content by hexane extraction.

TABLE 8

Average percent oil and protein of grain from the same experiment in comparisons of 31 fertile hybrid grain parents compared to sterile version of same hybrid pollinated by LP39 and LP39 (LG) (1994 Data).

| Pfister Hybrid | GDD to Silk* | Percent Oil Self Pollinated | Percent Oil LP39 TopCross | Percent Oil LP39 (LG) Topcross | Percent Protein Self Pollinated | Percent Protein LP39 TopCross | Percent Protein LP39 (LG) TopCross |
|---|---|---|---|---|---|---|---|
| X571 | 1073.5 | 4.86 | 7.59 | 7.97 | 10.43 | 13.57 | 12.67 |
| X529 | 1103.0 | 4.74 | 8.40 | 8.30 | 10.67 | 13.47 | 13.10 |
| 2020 | 1126.5 | 4.88 | 8.28 | 8.92 | 10.73 | 12.80 | 12.03 |
| X588 | 1153.0 | 4.45 | 8.10 | 8.39 | 11.30 | 11.63 | 12.23 |
| 2388 | 1174.5 | 5.01 | 7.50 | 7,74 | 13.17 | 14.83 | 14.40 |
| 3333 | 1191.0 | 4.89 | 7.72 | 7,73 | 12.67 | 13.57 | 13.63 |
| X577 | 1191.0 | 5.31 | 8.88 | 8.07 | 11.87 | 14.33 | 13.70 |
| X586 | 1205.0 | 5.15 | 8.20 | 9.20 | 13.07 | 13.73 | 14.80 |
| 2320 | 1205.0 | 5.02 | 8.62 | 8.30 | 12.07 | 15.10 | 14.00 |
| X592 | 1205.0 | 4.45 | — | 7.47 | 11.73 | — | 13.57 |
| 3000 | 1205.0 | 4.94 | 8.15 | 8.33 | 12.27 | 13.73 | 15.03 |
| X528 | 1205.0 | 5.02 | 7.75 | 7.46 | 12.23 | 12.83 | 12.87 |
| X527 | 1205.0 | 4.65 | 8.06 | 7.41 | 12.90 | 13.00 | 13.30 |
| 2375 | 1205.0 | 4.84 | 6.67 | 7.09 | 10.87 | 13.80 | 14.30 |
| X691 | 1222.5 | 4.93 | — | 7.69 | 11.83 | — | 13.03 |
| X570 | 1223.6 | 4.69 | 7.50 | 7.19 | 13.60 | 15.03 | 15.23 |
| X620 | 1223.5 | 5.15 | — | 7.86 | 11.77 | — | 12.80 |
| 2650 | 1244.0 | 4.41 | 7.02 | 7.31 | 12.07 | 13.37 | 13.20 |
| X594 | 1244.0 | 4.87 | — | 8.86 | 10.27 | — | 12.47 |
| 3030 | 1244.0 | 4.48 | — | 8.16 | 12.50 | — | 16.20 |
| 2725 | 1248.5 | 4.87 | 7.56 | 7.06 | 11.77 | 14.17 | 14.77 |
| 3339 | 1248.5 | 4.47 | 7.50 | 7.26 | 13.03 | 15.43 | 13.83 |
| X524 | 1248.5 | 5.00 | 7.82 | 7.50 | 13.63 | 13.40 | 14.37 |
| X518 | 1248.5 | 4.53 | 7.22 | 7.26 | 12.37 | 12.67 | 13.80 |
| 2417 | 1293.0 | 4.88 | 7.12 | 6.48 | 12.20 | 12.93 | 13.64 |
| X465 | 1293.0 | 4.44 | 6.79 | 7.32 | 12.34 | 14.53 | 14.10 |
| 3434 | 1293.0 | 5.04 | 7.53 | 7.91 | 12.50 | 14.80 | 13.53 |
| X574 | 1308.0 | 4.76 | — | 7.51 | 12.75 | — | 13.13 |
| X575 | 1308.0 | 4.79 | — | 7.88 | 10.53 | — | 12.80 |
| X600 | 1308.0 | 4.34 | — | 7.48 | 12.27 | — | 14.37 |
| X595 | 1308.0 | 4.91 | — | 8.40 | 10.73 | — | 13.77 |

TABLE 8-continued

Average percent oil and protein of grain from the same experiment in comparisons of 31 fertile hybrid grain parents compared to sterile version of same hybrid pollinated by LP39 and LP39 (LG) (1994 Data).

| Pfister Hybrid | GDD to Silk* | Percent Oil | | | Percent Protein | | |
|---|---|---|---|---|---|---|---|
| | | Self Pollinated | LP39 TopCross | LP39 (LG) Topcross | Self Pollinated | LP39 TopCross | LP39 (LG) TopCross |
| ASKC28 | 1248.5 | — | — | — | — | — | — |
| LP39 | 1174.5 | 13.25 | — | — | 12.30 | — | — |
| LP39(LG) | 1158.7 | 13.57 | — | — | 12.15 | — | — |
| Mean (for each column) | | 4.83 | 7.73 | 7.79 | 11.95 | 13.76 | 13.70 |
| **LSD (0.05) | | 0.16 | 0.45 | 0.27 | 1.36 | 1.69 | 1.74 |
| Stand. Dev. | | 0.25 | 0.57 | 0.61 | 0.97 | 0.94 | 0.93 |
| C.V. % (0.05) | | 2.05 | 3.50 | 2.09 | 6.96 | 7.43 | 7.79 |
| Mean (for three colums) | | | 6.75 | | | 13.11 | |
| **LDS (0.05) | | | 0.38 | | | 1.61 | |
| Stand. Dev. | | | 1.49 | | | 1.27 | |
| C.V. %(0.05) | | | 2.76 | | | 7.60 | |

\* - GDD determined from date of planting.
\*\* - LSD calculated at 0.05 confidence level according to Waller-Duncan K-ratio test with 8 replications.
FOOTNOTE: LP39 and LP39(LG) flowering over 18 days would adequately nick to pollinate hybrids up to 1205 GDD in northern cornbelt.

TABLE 9

Comparisons of fertile hybrid LP39 TopCross grain for GDD from pollination to 25, 20 and 15 percent grain moisture and relationship to dry down from same experiment (1994).

| Pfister Hybrid | Days to Pollination from Emergence | GDD to Pollination from Emergence | GDD from Emergence to Percent Grain Moisture | | | 25% Moisture | | | |
|---|---|---|---|---|---|---|---|---|---|
| | | | 25% | 20% | 15% | Oil % | % of GP | Protein % | % of GP |
| X571 | 54 | 983.5 | 2305.0 | 2354.5 | 2451.0 | 4.48 | — | 11.31 | — |
| X571-Sdms + X571 | 54 | 983.5 | 2305.0 | 2354.5 | 2451.0 | 4.29 | — | 11.73 | — |
| X571-Sdms + LP39 | 54 | 983.5 | 2329.5 | 2382.5 | 2367.0 | 8.05 | 187.64 | 11.80 | 100.60 |
| X571 + LP39 | 54 | 983.5 | 2305.0 | 2354.5 | 2455.0 | 8.04 | 179.46 | 12.19 | 107.78 |

TABLE 10

Comparison of three harvest dates for average percent oil of TopCross grain from hybrid LHE136Sdms x LH82 pollinated by LP39 from the same experiment (1993 data).

| Harvest Date | Oil % | St. Dev. | Protein % | St. Dev. | No. Reps |
|---|---|---|---|---|---|
| September 17 | 6.17 | 0.88 | 13.3 | 1.93 | 50 |
| September 19 | 6.24 | 0.87 | 12.4 | 1.51 | 50 |
| September 21 | 5.99 | 0.85 | 12.6 | 1.50 | 50 |

TABLE 11

Percent oil, protein and moisture at harvest across days commencing 35 days after pollination through 74 days after pollination for five maize genotypes (1994).

| Harvest Date | Days After Pollination | Pfister X571 | | | Pfister X571-Sdms-S | | | Pfister X571 LP39(LG) | | |
|---|---|---|---|---|---|---|---|---|---|---|
| | | Oil | Protein | Moist. % | Oil | Protein | Moist. % | Oil | Protein | Moist. % |
| Aug. | | | | | | | | | | |
| 12 | 35 | 4.64 | 12.50 | 55.0 | 4.40 | 12.27 | 56.0 | 7.33 | 12.23 | 52.5 |
| 16 | 39 | 4.72 | 11.27 | | 4.33 | 11.43 | | 7.60 | 11.80 | |
| 18 | 41 | 4.93 | 10.30 | | 4.50 | 9.70 | | 7.86 | 10.53 | |
| 20 | 43 | 4.44 | 10.80 | | 4.33 | 12.70 | | 7.56 | 14.57 | |
| 22 | 45 | 4.44 | 12.17 | | 4.62 | 12.73 | | 8.18 | 15.17 | |
| 24 | 47 | 4.83 | 12.30 | 43.0 | 4.41 | 12.73 | 44.0 | 7.80 | 12.47 | 44.0 |
| 26 | 49 | 4.87 | 12.03 | | 4.19 | 13.20 | | 8.58 | 13.10 | |
| 28 | 51 | 4.20 | 9.57 | | 4.50 | 9.57 | | 7.94 | 13.17 | |
| 29 | 52 | 4.40 | 10.13 | 37.0 | 4.24 | 11.90 | 39.0 | 8.83 | 14.73 | 37.0 |
| 30 | 53 | 4.63 | 11.57 | | 4.77 | 12.03 | | 8.85 | 12.20 | |
| Sept. | | | | | | | | | | |
| 1 | 54 | 4.76 | 12.53 | 35.0 | 4.03 | 10.30 | 36.0 | 8.55 | 12.27 | 36.0 |
| 3 | 56 | 4.40 | 11.27 | | 4.66 | 10.40 | | 9.62*** | 12.33 | |
| 5 | 58 | 4.69 | 12.40 | | 4.16 | 11.93 | | 8.45 | 15.33 | |
| 7 | 60 | 4.27 | 10.93 | | 4.47 | 11.97 | | 9.16 | 13.13 | |
| 9 | 62 | 4.32 | 11.07 | 31.0 | 4.51 | 10.83 | 27.5* | 8.97 | 10.30 | 32.0 |
| 11 | 64 | 4.04 | 11.90 | 26.0* | 4.18 | 11.13 | | 8.33 | 11.03 | 26.0* |
| 12 | 65 | 4.39 | 12.60 | 28.0 | 4.29 | 11.70 | 26.0 | 8.85 | 11.03 | 27.0 |
| 15 | 68 | 4.08 | 10.33 | 23.0 | 4.36 | 12.00 | 24.0 | 8.70 | 14.57 | 21.0 |
| 17 | 70 | 4.13 | 13.47 | | 4.33 | 12.37 | | 8.18 | 10.53 | |
| 19 | 72 | 4.48 | 11.31 | 17.0 | 4.29 | 11.73 | 17.0 | 8.04 | 12.19 | 19.0 |
| 21 | 74 | 4.32 | 12.20 | 17.0 | 4.67 | 11.60 | 17.0 | 8.47 | 13.90 | 19.0 |
| Mean | | 4.48 | 11.57 | | 4.40 | 11.63 | | 8.06 | 12.72 | |
| LDS | | 0.46 | 0.34 | | 0.61 | 0.30 | | 2.70 | 0.38 | |
| Stand. Dev. | | 0.27 | 1.01 | | 0.19 | 1.02 | | 0.83 | 1.60 | |
| C.V. % | | 6.20 | 1.78 | | 8.45 | 1.59 | | 20.24 | 1.80 | |
| Oil Range Sept. 19 | | 3.70–5.41 | | **(97) | 3.35–5.31 | | (81) | 6.58–10.25 | | (100) |

| | Pfister X571-Sdms LP39(LG) | | | LP39(LG)-Sib | | | GDD from |
|---|---|---|---|---|---|---|---|
| Harvest Date | Oil | Protein | Moist. % | Oil | Protein | Moist. % | Flowering to Harvest |
| Aug. | | | | | | | |
| 12 | 7.75 | 13.47 | 55.0 | 13.95 | 10.23 | 46.0 | 714.5 |
| 16 | 8.34 | 11.10 | | 13.09 | 12.87 | | 781.0 |
| 18 | 8.10 | 10.30 | | 12.88 | 9.97 | | 816.0 |
| 20 | 8.51 | 12.70 | | 15.28 | 13.10 | | 859.0 |
| 22 | 8.17 | 11.73 | | 13.99 | 12.37 | | 890.5 |
| 24 | 7.72 | 13.33 | 43.0 | 14.80 | 16.17 | 36.0 | 933.5 |
| 26 | 7.91 | 13.27 | | 13.67 | 15.13 | | 980.5 |
| 28 | 8.68 | 13.57 | | 14.39 | 13.77 | | 1023.0 |
| 29 | 8.39 | 12.67 | 37.0 | 14.01 | 10.00 | 37.0 | 1037.0 |
| 30 | 8.33 | 12.20 | | 15.59 | 14.30 | | 1047.0 |
| Sept. | | | | | | | |
| 1 | 8.13 | 11.80 | 35.0 | 14.91 | 9.37 | 36.0 | 1066.5 |
| 3 | 8.54 | 10.73 | | 14.76 | 11.97 | | 1090.0 |
| 5 | 8.12 | 11.10 | | 15.84 | 17.30 | | 1105.5 |
| 7 | 8.82 | 12.50 | | 12.12 | 11.87 | 32.0* | 1133.5 |
| 9 | 8.48 | 11.30 | 30.0 | 14.42 | 16.37 | 33.0 | 1169.5 |
| 11 | 9.09*** | 11.07 | | 15.02 | 13.77 | | 1214.5 |
| 12 | 8.04 | 9.87 | 26.0* | 16.41*** | 14.20 | 30.0 | 1236.0 |
| 15 | 7.54 | 11.20 | 25.5 | 12.19 | 11.17 | 28.0 | 1306.0 |
| 17 | 7.23 | 11.07 | | 13.89 | 14.27 | | 1343.5 |
| 19 | 7.77 | 11.72 | 16.0 | 13.57 | 12.15 | 25.0 | 1377.5 |
| 21 | 6.96 | 9.30 | 16.0 | 13.82 | 13.60 | 25.0 | 1414.0 |
| Mean | 8.14 | 11.71 | | 14.28 | 13.04 | | |
| LDS | 0.76 | 0.35 | | 1.12 | 0.99 | | |

TABLE 11-continued

Percent oil, protein and moisture at harvest across days commencing 35 days after pollination through 74 days after pollination for five maize genotypes (1994).

|  |  |  |  |  |  |  |
|---|---|---|---|---|---|---|
| Stand. Dev. | 0.52 | 1.22 |  | 1.16 | 2.33 |  |
| C.V. % | 5.67 | 1.81 |  | 4.75 | 4.58 |  |
| Oil Range | 5.62–9.46 |  | (100) | 10.58–16.16 |  | (98) |
| Sept. 19 |  |  |  |  |  |  |

*Date of black layer, physiological maturity.
**Number of entries
***Date of maximum oil The oil contents of grain produced in first year strip tests of Pfister male sterile hybrids X571 and 3000 pollinated by LP39 are given in Table 3. Comparisons of these oil contents to the oil contents of the grain from the fertile checks of these hybrids revealed about a 2% net increase in oil (6.49% compared to 4.66% for Pfister Hybrid X571 and 6.31% compared to 4.38% for Pfister Hybrid 3000 in tests made at El Paso, Ill.).

In second year comparisons, the oil content of grain produced by male sterile Pfister hybrids X529, X571, X577, X586, 2020, 3000 and 3034 pollinated by LP39 showed a 2.6% mean increase in oil compared to the oil content of the grain produced by the fertile hybrid checks (7.0% compared to 4.4%, Table 5).

TopCross™ grain expressed a mean increase of 2.58% oil (7.53% compared to 4.95%, Table 6) and 2.90% oil (7.73% compared to 4.83%, Table 8), respectively, in first and second year trials across an array of 22 hybrid male sterile grain parents pollinated by LP39 when compared against the grain produced by fertile hybrid checks in the same experiment.

The oil content of TopCross™ grain was not significantly different across multiple harvest dates within the same experiment (Table 10).

A comparison was made of the oil content of the grain obtained from LP39 single crosses and from LP39A×LP39B intercrosses crossed to Pfister hybrid 3000. The results of this comparison are presented in Table 4 above. The mean oil content of the grain was 5.97% from LP39 single crosses and 6.31% from LP39A×LP39B intercrosses, indicating a slight advantage for the intercross pollinators.

In first year trials with late generation LP39, hybrid strip test comparisons for oil content were made between grain produced from male sterile Pfister hybrids X529, X571, X586, 2020 and 3034 pollinated by late generation LP39 and grain produced from the fertile hybrid checks ("Hybrid Self") (Table 5).

The oil content of the grain produced from the male sterile Pfister hybrids pollinated by late generation LP39 and the grain produced from fertile hybrid checks was calculated by two different methods of oil analysis: wet chemistry analysis of an independent laboratory against NIR analysis. These results are provided in Tables 5 and 7.

Comparisons of the relationship of oil and starch contents of grain produced by male sterile Pfister hybrids X529, X571, X586, 2020 and 3034 pollinated by LP39 to grain produced by the fertile hybrids revealed that oil increased in an inverse relationship to starch. For example, in comparing grain produced from fertile Pfister hybrid X571 to grain produced from X571 pollinated by late generation LP39, oil content increased (from 4.39% to 8.05%) while starch content decreased (from 71% to 64%) (Table 7).

A comparison of the oil content of grain produced from late generation LP39 crossed to 31 male sterile grain parent hybrids against grain produced from the fertile hybrids revealed that late generation LP39 increased oil of TopCross™ grain by 2.96% (7.79% compared to 4.83%), as shown in Table 8 above.

A comparison of the oil content at 25% grain moisture of grain produced from Pfister hybrids X571 and X571-Sdms pollinated by late generation LP39 and grain produced from fertile hybrid X571 and X571-Sdms pollinated by X571 are presented in Table 9 above. Oil content was highest in the grain produced from Pfister hybrids X571 and X571-Sdms pollinated by late generation LP39 (8.04% and 8.05% respectively).

Table 11 above shows the oil content of grain produced from hybrids X571 and X571-Sdms pollinated by X571 (columns one and two) and grain produced from Pfister hybrids X571 and X571-Sdms pollinated by LP39 (columns three and four), where the grain was harvested 35 days after flowering and then harvested on alternate days to and beyond the onset of physiological maturity (i.e., black layer). Pfister hybrid X571-Sdms pollinated by LP39 expressed 7.75% in oil content of the grain as early as 715 GDD after flowering, thus indicating a very high level of oil while the plant foliage was green and actively growing, hence permitting an early harvest for silage and/or earlage.

Silage comparisons of Pfister hybrids X571 and X586 pollinated by LP39 to the fertile hybrids are presented in Table 12. The high oil corn silage from the LP39 pollination provides greater total digestible nutrients (TDN) to the animal ration, thus permitting greater flexibility in animal feed formulation and increasing productivity per acre for each cow, resulting in increased beef and butterfat production.

TABLE 12

High Oil TopCross Silage Evaluation — Percent Dry Weight Basis

| Hybrid | % Moisture | Protein | Fat* | % Increase | ADF* | NDF* | ASH | NEL* M Cal/lb. | % Increase | TDN* | % Increase | Locations |
|---|---|---|---|---|---|---|---|---|---|---|---|---|
| Pfister X571 + LP39 | 56.78 | 7.48 | 5.55b | 172 | 21.86 | 41.66c | 4.96 | 0.74c | 106 | 72.69b | 104 | 10 |
| Pfister X571 | 50.70 | 7.47 | 3.22a |  | 24.34 | 48.49a | 5.45 | 0.69b |  | 69.73a |  | 7 |
| Pfister X586 + LP39 | 52.58 | 7.87 | 6.62c | 197 | 23.80 | 45.54b | 5.04 | 0.74c | 108 | 73.28b | 106 | 9 |

TABLE 12-continued

High Oil TopCross Silage Evaluation — Percent Dry Weight Basis

| Hybrid | % Moisture | Protein | Fat* | % Increase | ADF* | NDF* | ASH | NEL* M Cal/lb. | % Increase | TDN* | % Increase | Locations |
|---|---|---|---|---|---|---|---|---|---|---|---|---|
| Pfister X586 | 54.74 | 8.53 | 3.36a | | 26.03 | 50.01a | 5.20 | 0.68b | | 69.17a | | 9 |
| Pfister 3000 + ASKC28 | 61.02 | 8.35 | 6.01b | 181 | 24.41 | 46.50b | 4.56 | 0.74c | 118 | 72.92b | 104 | 14 |
| Pfister 3000 | 52.91 | 7.98 | 3.32a | | 25.40 | 49.00a | 4.40 | 0.63a | | 70.32a | | 9 |
| Stand. Dev. | | 1.00 | 0.58 | | 1.75 | 2.66 | 0.49 | 0.010 | | 0.68 | | |

*ADF, Acid Detergent Fiber; NDF, Non-Digestible Fiber; NEL, Net Energy for Lacation; TDN, Total Digestible Nutrients. Within a column, values followed by different letters are significantly different at the 0.05 percent level.
Silage evaluation was provided by Midwest Laboratories, Inc., 13611 B Street, Omaha, Nebraska. 68144-3693, Tele. 1-402-334-7770, FAX 1-402-334-9121.

Example III

Protein of TopCross™ Grain

Protein comparisons are presented in Tables 5, 6, 7, 8, 9, 10, 11 and 12 above. Protein contents of TopCross™ grain were observed to vary between environments, methods of laboratory analysis, harvest date and by genotype of grain parent.

Protein content of TopCross™ grain resulting from the pollination by LP39 of male sterile Pfister hybrids X529, X571, X577, X586, 2020, 3000 and 3034 was compared to the protein content of grain from open pollinated fertile hybrid checks (Table 5). In strip tests, analysis of population means of protein indicated LP39 significantly increased protein of TopCross™ grain (Table 5). For example, at the Evansville test site, protein content was higher in the grain from X586 pollinated by LP39 (9.4%) than grain from the fertile X586 check (8.5%), representing an improvement of 0.9%.

In multiple year (1993 and 1994) comparisons of protein from arrays of 22 and 31 sterile grain parents respectively pollinated by LP39, the population mean of TopCross™ grain protein content from LP39 was significantly greater than the population mean of self pollinated fertile hybrid grain parents (13.48% compared to 11.69% in 1993 (Table 6) and 13.76% compared to 11.95% in 1994 (Table 8).

Protein content of TopCross™ grain resulting from the pollination by LP39 of male sterile Pfister hybrids X529, X571, X586, 2020 and 3034 was compared to protein content of grain from self pollinated fertile hybrids by analyzing the grain at two different laboratories. TopCross™ grain was found to express a mean increase of 0.6% (9.1% compared to 8.5%, Table 5) and 1.8% (Table 7), respectively, from these protein analyses by the two different laboratories.

Comparisons of the protein content of grain resulting from the pollination of 31 male sterile hybrid grain parents by late generation LP39 to the protein content of grain from fertile hybrids revealed a mean increase of 1.75% protein (13.70% compared to 11.95%, Table 8). Comparisons of protein content of grain from male sterile and fertile hybrids X571 pollinated by late generation LP39 against grain from male sterile and fertile hybrids pollinated by X571 are presented in Table 9. Grain from these same hybrids were compared for protein across 21 harvest dates that commenced 35 days after flowering and continued on alternate dates to the date of physiological maturity and beyond (Table 11).

Example IV

Moisture of TopCross™ Grain

Conventional high oil hybrids traditionally express higher grain moisture at harvest and are slower to dry down than lower-oil dent hybrids of the same maturity. To test this concept of higher moisture associated with higher oil content of grain, comparisons were made of moisture at harvest of grain resulting from the pollination by LP39 of male sterile Pfister hybrids X529, X571, X577, X586, 2020, 3000 and 3034 to grain resulting from the self pollination of comparable fertile Pfister hybrids. Relative grain moisture was determined by an electronic moisture tester that had been previously calibrated for high oil corn against the Brown-Duvel Moisture tester which utilizes a distillation process. This moisture data is found in Tables 3, 4, 5, 9, 11, 12 and in Table 13 below.

TABLE 13

Relative grain moisture of two grain parent hybrids utilized in LP39 TopCross experiment harvested at alternate intervals commencing 35 days after pollination and harvested at sequential dates to determine GDD to 25 percent grain moisture (1994).*

| | Percent Grain Moisture — Date | | | | | | | | | | | | Black Layer |
|---|---|---|---|---|---|---|---|---|---|---|---|---|---|
| Pfister Hybrid | Aug. 12 | Aug. 17 | Aug. 24 | Aug. 29 | Sept. 1 | Sept. 6 | Sept. 9 | Sept. 12 | Sept. 13 | Sept. 15 | Sept. 16 | Sept. 21 | Date/ Moist. |
| Pfister Hybrid X571 | 55.0 | 48.0 | 43.0 | 37.0 | 35.0 | 32.0 | 31.0 | 28.0 | 27.0 | 23.0 | | 17.0 | 9/11 - 26.0 |
| Pfister Hybrid X571Sdms-S | 56.0 | 49.5 | 44.0 | 39.0 | 36.0 | 32.0 | 27.5 | 26.0 | 27.0 | 24.0 | | 17.0 | 9/9 - 27.5 |
| (Pfister Hybrid X571)LP39(LG) | 52.5 | 50.5 | 44.0 | 37.0 | 36.0 | 34.0 | 32.0 | 27.0 | 28.5 | 21.0 | | 19.0 | 9/11 - 26.0 |
| (Pfister Hybrid X571Sdms)LP39(LG) | 55.0 | 49.0 | 43.0 | 37.0 | 35.0 | 33.0 | 30.0 | 26.0 | 26.5 | 25.5 | | 16.0 | 9/12 - 26.0 |
| LP39-Sib | 46.0 | 42.5 | 36.0 | 37.0 | 36.0 | 34.0 | 33.0 | 30.0 | 30.0 | 28.0 | 25.0 | 25.0 | 9/7 - 32.0 |

*Percent oil and percent protein data is presented on Table 15 for each of these respective dates. Relative grain moisture was determined by distillation on a Brown-Duvel Moisture Tester.

Grain moisture of LP39 TopCross™ grain was −3.0%, −1.4% and −3.0% lower in moisture, respectively, than fertile grain parent checks X571 and 3000 at El Paso and X571 at Janesville locations (Table 3). Grain moisture comparisons of population means of seven hybrids pollinated by LP39 were made against fertile hybrids and these results revealed no major differences in grain moisture (Table 5). Comparisons of GDD to 25, 20 and 15 percent grain moisture of TopCross™ grain of Pfister X571-Sdms were made against self pollinated Pfister X571 and the results, as presented in Table 9, indicate no major GDD differences between grain resulting from the pollination by LP39 of male sterile hybrids and grain resulting from the self pollination of fertile hybrids relative to GDD for specific moisture levels of TopCross™ grain. These results are illustrated in more detail in Tables 11 and 13 which present the rate of dry-down across a period of 40 days (August 12 to September 21) starting at 35 days after flowering to physiological maturity (i.e., black layer).

Example V

Density of TopCross™ Grain

Comparisons of the density of TopCross™ grain resulting from the pollination by LP39 of male sterile Pfister hybrids X529, X571, X586, 2020 and 3034 were made against the density of grain resulting from the self pollination of the comparable fertile hybrids (Table 7). Test weight and 50 kernel weight comparisons of TopCross™ grain from Pfister hybrids X571 and 3000 were also made against fertile hybrids (Table 3).

Additional TopCross™ grain density comparisons are presented in Table 5. As Table 5 shows, there were no major differences in the grain density of LP39 and late generation LP39 TopCross™ grain compared to the grain density of self pollinated fertile hybrids.

In other comparisons, LP39 and late generation LP39 TopCross™ grain density were significantly improved when compared to TopCross™ grain produced by the pollination of ASKC28 in 83 and 74 percent of the hybrids, respectively, in tests of 23 different grain parents. There were no major differences in grain density of LP39 and late generation LP39 TopCross™ grain compared to grain density of self pollinated fertile hybrids (Table 14 below):

TABLE 14

Average density of grain from the same experiment in comparisons of 23 fertile hybrid grain parents compared to sterile version of same hybrid pollinated by LP39, LP39(LG), and ASKC28 (1994 data).

| Hybrid | Density—gm/ml | | | |
| --- | --- | --- | --- | --- |
| | Self Pollinated | LP39 TopCross | LP39(LG) TopCross | ASKC28 Topcross |
| X571 | 1.20 | 1.22 | 1.22 | 1.21 |
| X529 | 1.24 | 1.23 | 1.25 | 1.17 |
| 2020 | 1.23 | 1.24 | 1.24 | 1.14 |

TABLE 14-continued

Average density of grain from the same experiment in comparisons of 23 fertile hybrid grain parents compared to sterile version of same hybrid pollinated by LP39, LP39(LG), and ASKC28 (1994 data).

| Hybrid | Density—gm/ml | | | |
| --- | --- | --- | --- | --- |
| | Self Pollinated | LP39 TopCross | LP39(LG) TopCross | ASKC28 Topcross |
| X588 | 1.25 | 1.24 | 1.27 | 1.24 |
| 2388 | 1.23 | 1.22 | 1.23 | 1.19 |
| 3333 | 1.23 | 1.23 | 1.21 | 1.20 |
| X577 | 1.22 | 1.23 | 1.22 | 1.23 |
| X586 | 1.24 | 1.24 | 1.24 | 1.20 |
| 2320 | 1.23 | 1.24 | 1.23 | 1.20 |
| 3000 | 1.23 | 1.24 | 1.23 | 1.21 |
| X528 | 1.22 | 1.21 | 1.21 | 1.15 |
| X527 | 1.21 | 1.20 | 1.20 | 1.17 |
| 2375 | 1.22 | 1.22 | 1.23 | 1.16 |
| X570 | 1.23 | 1.21 | 1.24 | 1.17 |
| 2650 | 1.24 | 1.23 | 1.27 | 1.18 |
| 3030 | 1.23 | 1.23 | 1.24 | 1.17 |
| 2725 | 1.20 | 1.20 | 1.19 | 1.19 |
| 3339 | 1.23 | 1.24 | 1.22 | 1.19 |
| X524 | 1.20 | 1.17 | 1.20 | 1.14 |
| X518 | 1.23 | 1.24 | 1.23 | 1.18 |
| 2417 | 1.22 | 1.21 | 1.18 | 1.17 |
| X465 | 1.20 | 1.18 | 1.20 | 1.14 |
| 3434 | 1.22 | 1.21 | 1.21 | 1.17 |
| Mean (for each column) | 1.22 | 1.22 | 1.22 | 1.18 |
| LSD (0.05) | 0.00 | 0.00 | 0.00 | 0.00 |
| Stand. Dev. | 0.01 | 0.02 | 0.02 | 0.03 |
| C.V. % (0.05) | 0.00 | 0.00 | 0.00 | 0.00 |
| Mean (for four columns) | 1.21 | | | |
| LSD (0.05) | 0.02 | | | |
| Stand. Dev. | 0.03 | | | |
| C.V. % (0.05) | 0.00 | | | |

Example VI

Tassel-Silk Synchronization

The success of the TopCross™ grain production system is primarily based on the synchronization of pollen shed from the pollinator with the extrusion of silks from the male sterile grain parent hybrid, which is termed nicking. Tables 3, 4, 6, 8, 9 and Tables 15 and 16 below present results of these nicking comparisons and show how different environments may influence the timing of nicking.

TABLE 15

LP39(LG)
Pollen Production — Weight (gm) per 5 plants
Date — July, 1994

| Replicate | 6 | 7 | 8 | 9 | 10 | 11 | 12 | 13 | 14 | 15 | Total Pollen Wt. (gms) |
|---|---|---|---|---|---|---|---|---|---|---|---|
| I | 4.538 | 5.453 | 6.160 | 3.207 | 2.891 | 1.662 | 1.354 | 0.405 | 0.033 | 0.000 | 25.704 |
| II | 3.984 | 4.743 | 4.255 | 2.824 | 3.991 | 2.726 | 2.074 | 1.087 | 0.064 | 0.005 | 25.753 |
| Mean | 4.261 | 5.098 | 5.207 | 3.021 | 3.441 | 2.194 | 1.714 | 0.746 | 0.048 | 0.002 | 25.728 |
| Mean pollen weight (gms) of pollen produced per plant | | | | | | | | | | | 5.146 gm. |

NOTE: Pollen collected at 11:00 A.M. at daily intervals from individual tassels that were covered by a paper bag receptacle from initial pollen shedding date to final pollen shed over 10-days across an array of 5 plants in each replicate to determine the average amount of pollen by weight that was produced by each LP39 plant.

TABLE 16

Frequency distribution of duration of tassel shedding period for LP39(LG) and the frequency distribution of silk extrusion dates in 1994.

| | Date Percent of Population | | | | | | | | | | |
|---|---|---|---|---|---|---|---|---|---|---|---|
| | June 29 | June 30 | July 1 | July 2 | July 3 | July 4 | July 5 | July 6 | July 7 | July 8 | July 9 |
| Starting Shedding Date | 1.4 | 4.1 | 0.3 | 14.8 | 14.5 | 24.9 | 20.0 | 11.0 | 4.9 | 1.2 | 1.4 |
| Last Shedding Date | | | | | | | 0.5 | 0.0 | 4.1 | 27.5 | 23.8 |
| Silk Extrusion Date | | | | | | 8.1 | 17.7 | 24.3 | 20.3 | 11.6 | 5.5 |

| | Date Percent of Population | | | | | | | Total | |
|---|---|---|---|---|---|---|---|---|---|
| | July 10 | July 11 | July 12 | July 13 | July 14 | July 15 | July 16 | Dead | Plants Observed |
| Starting Shedding Date | 0.6 | | | | | | | 0.9 | 345 |
| Last Shedding Date | 19.0 | 10.7 | 5.2 | 4.1 | 2.0 | 2.0 | 0.3 | 0.8 | 345 |
| Silk Extrusion Date | 9.3 | 0.6 | | | | | | 10.6 | 345 |

Summary: LP39 50 percent pollen shedding date and silk extrusion date was July 6 which resulted from an accumulation of 1014.0 GDD and compared to grain parent Pfister X571 in the same experiment that expressed 50 percent silk extrusion on July 8 which resulted from an accumulation of 1070.2 GDD.

Comparisons of the mid-tassel shedding date of LP39 with the mid-silking date of Pfister X571-Sdms revealed that the LP39 mid-tassel date was 18.5 GDD earlier than the Pfister hybrid X571-Sdms mid-silking date (1147.5 GDD compared to 1166.0 GDD, Table 3) which was interpreted as approximately three-fourths of a day. The LP39 mid-tassel date was 115.5 GDD earlier than the Pfister hybrid 3000-Sdms mid-tassel date (1147.5 GDD compared to 1263 GDD, Table 3) which represents about four days.

In Table 6, GDD to silk flowering are given for 22 hybrids and LP39 (1993 data). In Table 8, GDD to silk flowering are given for 31 hybrids and for ASKC28, LP39 and late generation LP39 (1994 data).

The pollination period of LP39 extended over 18 days with peak pollen production occurring about eight days after initial pollen shed of the population (Table 16).

Example VII

Random Amplified Polymorphic DNA (RAPD) Data and Polymorphic Markers in Maize Related to LP39

A total of 168 random amplified polymorphic DNA (RAPD) and polymorphic markers were used to establish the degree of relationship of LP39 to its genetic oil source ASKC28 along with related synthetic normal starch grain synthetic oil populations ASKC20 and UHOC3 and to the dent inbred parents of LP39. The results are presented in Table 17 below:

TABLE 17

Analysis of random amplified polymorphic DNA (RAPD) markers for classification of synthetic oil populations into polymorphic groups on the basis of identification af 168 DNA bands from each line and their respective percentage differences from the maize line in a comparison.*

| Maize Line | PERCENTAGE DIFFERENCE OF MAIZE LINE COMPARED TO: | | | | | |
|---|---|---|---|---|---|---|
| | LP39 | LP39A | LP39B | LH51 | LH132 | LP39(LG) |
| LP39 | 0.0 | 21.6 | 26.0 | 37.4 | 27.2 | 32.7 |
| LP39A | 21.6 | 0.0 | 13.6 | 36.1 | 28.5 | 29.3 |
| LP39B | 26.0 | 13.6 | 0.0 | 35.6 | 36.2 | 30.1 |
| LH51 | 37.4 | 36.1 | 35.6 | 0.0 | 35.7 | 39.3 |
| LH82 | 20.6 | 29.7 | 35.7 | 37.0 | 25.3 | 41.2 |
| LH132 | 27.2 | 28.5 | 36.2 | 35.7 | 0.0 | 36.2 |
| NC282 | 36.4 | 35.8 | 47.1 | 36.9 | 14.0 | 40.4 |
| ASK C28 | 25.5 | 21.5 | 22.4 | 32.1 | 35.2 | 31.4 |
| ASK C20 | 26.0 | 30.9 | 33.5 | 41.5 | 26.8 | 32.9 |
| UHOC3 | 30.3 | 21.7 | 21.7 | 43.9 | 33.5 | 26.7 |

*The RAPD markers were located every 15 cm for a genome size of 2500 cm. For example, in the first comparison, LP39 is 0.0 percent different than itself and LP39A is 21.6 percent different than LP39, etc.

This genetic map assumes RAPDs are dominant markers and each marker is controlled by a single locus. The segregation of these markers followed a biparental diploid mode of inheritance. This data unambiguously reveals the distinctiveness and differences of each of the maize populations (left hand side of Table 17) compared to LP39, its LP39A and LP39B parents, their genetic background sources LH132 and LH51, and late generation LP39.

Genotype data was generated for five synthetic oil populations based on an analysis of 29 RAPD markers at loci from eight linkage groups having a significant effect on oil. The results are shown in Table 18 below:

Rockville, Md. 20852, ATCC Deposit No. 97023 the deposit having been made on Jan. 12, 1995. The seeds deposited with the ATCC are taken from the same deposit maintained by Pfister Hybrid Corn Company, Box 187, 187 North Fayette Street, El Paso, Ill. 61738, since prior to the filing date of this application. The deposit will be maintained in the

TABLE 18

Genotype of five synthetic oil populations based on analysis of 29 RAPD markers at loci from eight linkage groups having a significant effect on oil.

| RAPD Marker | Linkage Group | Percent of Oil Variation | Synthetic Oil Populations* | | | | |
|---|---|---|---|---|---|---|---|
| | | | LP39 | ASKC28 | ASKC20 | UHOC3 | LP39(LG) |
| m30F8.A | 1 | 27.1 | + | + | + | + | + |
| m23H6.A** | | 18.2 | − | + | + | + | − |
| m11G7.C | | 15.9 | + | + | + | + | + |
| m16A10.A | | 16.6 | + | + | + | + | + |
| m22F11.A | | 17.7 | + | + | + | + | + |
| m27H7.B | 3 | 3.0 | + | + | + | + | + |
| m32B3.A | | 1.3 | + | + | + | + | + |
| m13E6.A | | 2.3 | + | + | + | + | + |
| m28D9.A | | 2.0 | + | + | + | + | + |
| m33D9.A | 5 | 1.4 | + | + | + | + | + |
| m26F8.A | | 1.9 | + | − | + | + | + |
| m31G12.A | | 1.3 | + | + | + | + | + |
| m13F8.B | | 1.4 | + | + | + | + | + |
| m13D6.A | | 1.4 | + | + | + | + | + |
| m21B2.A | | 1.6 | + | + | + | + | + |
| m26C10.A | 7 | 0.2 | + | + | + | + | + |
| m16H7.B | | 2.2 | + | + | + | + | + |
| m12B2.B | | 0.4 | + | + | − | + | + |
| m12E5.B*** | 9 | 3.1 | − | + | + | + | + |
| m16A3.A | | 1.8 | + | + | + | + | + |
| m33A9.B | | 0.2 | + | + | + | + | + |
| m33C9.A | 11 | 3.2 | + | + | + | + | + |
| m14G5.A*** | | 4.2 | − | + | + | − | + |
| m30F5.A | | 5.4 | + | + | + | + | + |
| m33A9.A | | 3.1 | + | + | + | + | + |
| m17F3.B | 12 | 2.1 | + | + | + | + | + |
| m34A4.A | | 1.5 | + | + | + | + | + |
| m18E2.A | | 1.2 | + | + | + | + | + |
| m32B5.A | | 2.0 | + | + | + | + | + |

*"+" indicates presence of an ASKC28 allele +/+ or +/− at the locus and "−" indicates absence of an ASKC28 allele (−/−) at the locus.
**Major oil gene not present in LP39 and LP39(LG).
***Minor oil gene not present in LP39 and present in LP39(LG).

Random amplified polymorphic DNA analysis of synthetic hybrid LP39 and related maize populations was provided by Scott V. Tingey and Mark Jung of E. I. DuPont de Nemours and Company Inc., Agricultural Products Department, Experimental Station 402/4249, P.O. Box 80402, Wilmington, Del. 19880-0402 (tele. 1-302-695-4216; FAX 1-302-695-4296). Use of RAPD technology and DNA polymorphic markers was presented according to procedures described in: (1) Williams, J. G. K., J. A. Rafalski and S. V. Tingey, *Genetic Analysis Using RAPD Markers In: Methods In Enzymology*, Orlando, Fla., USA. Academic Press (1991); (2) Rafalski, J. A., S. V. Tingey and J. G. K. Williams, *RAPD Markers—A New Technology For Mapping And Plant Breeding*, AgBiotech News and Information, V. 3 No. 4, pp 645–648 (1991); and (3) Tingey, S. V. and J. P. del Tufo, *Genetic Analysis With Random Amplified Polymorphic DNA Markers*, Plant Physiol., 101:349–352 (1993).

Deposit Information

Applicant has made available to the public without restriction a deposit of at least 2500 seeds of synthetic hybrid LP39 with the American Type Culture Collection (ATCC), ATCC depository, which is a public depository, for a period of 30 years, or 5 years after the most recent request, or for the effective life of the patent, whichever is longer, and will be replaced if it becomes nonviable during that period. LP39A and LP39B were deposited with the ATCC on Aug. 27, 1996 and were assigned ATCC Deposit Nos. 97696 and 97697 respectively. ASKC28 has been previously deposited with the ATCC. LH132, NC282 and LH51 are publicly available materials.

Although the foregoing invention has been described in some detail by way of illustration and examples for purposes of clarity and understanding, it will be obvious that certain modifications and alternative embodiments of the invention are contemplated which do not depart from the spirit and scope of the invention as defined by the foregoing teachings and appended claims.

What is claimed is:

1. A synthetic hybrid corn seed designated LP39 and having ATCC Accession No. 97023, or any corn line derived therefrom.

2. A synthetic hybrid corn plant and its parts produced by the seed of claim 1.

3. Corn plants regenerated from tissue culture of the synthetic hybrid corn plants of claim 2.

4. Pollen of the synthetic hybrid corn plant of claim 2.

5. Tissue culture according to claim 3 comprising regenerable cells of a plant part selected from the group consisting of meristematic tissue, anthers, leaves, embryos, protoplasts, and pollen.

6. A corn plant regenerated from regenerable cells of a tissue culture according to claim 5.

7. A synthetic hybrid corn plant having all the phenotypic, genotypic and physiological characteristics of the seed of claim 1.

8. A method for producing a synthetic hybrid corn seed having the designation of LP39 and comprising the steps of:

a) planting in pollinating proximity seeds of corn synthetic lines LP39A and LP39B;

b) cultivating corn plants resulting from the planting until the time of flowering;

c) emasculating the flowers of the plants of either synthetic line;

d) allowing natural cross pollination to occur between the synthetic lines; and e) harvesting seeds produced on the emasculated plants of the synthetic line.

9. A synthetic hybrid corn plant and seed thereof produced by crossing a synthetic corn plant according to claim 2 with another, different corn plant and having one half of the nuclear genotype of the synthetic corn plant of claim 2.

10. Corn grain produced by the process of:

(a) planting, in pollinating proximity, seeds of synthetic hybrid corn plant LP39 and seeds of a male sterile corn hybrid;

(b) cultivating corn plants resulting from the planting;

(c) allowing the LP39 corn plants to pollinate the male sterile hybrid corn plants;

(d) harvesting the resulting corn grain from all plants.

11. Synthetic corn seed designated LP39A and having ATCC Accession No. 97696.

12. Synthetic corn seed designated LP39B and having ATCC Accession No. 97697.

* * * * *

UNITED STATES PATENT AND TRADEMARK OFFICE
CERTIFICATE OF CORRECTION

PATENT NO. : 5,675,065
DATED : October 7, 1997
INVENTOR(S) : Richard R. Bergquist It is certified that error appears in the above-indentified patent and that said Letters Patent is hereby corrected as shown below:

```
In Table 6, column 28, line 39:
 "X518  1286   4.68  6.93   11.3  13.8  9" should read
-- X518  1285   4.68  6.93   11.3  13.8  9 --

In Table 8, column 29:
 "2388  1174.5  5.01  7.50   7,74  13.17 14.83 14.40" should read
-- 2388  1174.5  5.01  7.50   7.74  13.17 14.83 14.40 --

"3333  1191.0  4.89  7.72   7,73  12.67 13.57 13.63" should read
-- 3333  1191.0  4.89  7.72   7.73  12.67 13.57 13.63 --

"X691  1222.5  4.93   -     7.69  11.83   -   13.03" should read
-- X591  1222.5  4.93   -     7.69  11.83   -   13.03 --

"X570  1223.6  4.69  7.50   7.19  13.60 15.03 15.23" should read
-- X570  1223.5  4.69  7.50   7.19  13.60 15.03 15.23 --
```

Signed and Sealed this

Twenty-fourth Day of February, 1998

Attest:

BRUCE LEHMAN

Attesting Officer     Commissioner of Patents and Trademarks